US011127721B2

(12) United States Patent
Li et al.

(10) Patent No.: US 11,127,721 B2
(45) Date of Patent: Sep. 21, 2021

(54) FULL SPECTRUM WHITE LIGHT EMITTING DEVICES

(71) Applicant: Intematix Corporation, Fremont, CA (US)

(72) Inventors: Yi-Qun Li, Danville, CA (US); Xianglong Yuan, Manteca, CA (US); Jun-Gang Zhao, Fremont, CA (US)

(73) Assignee: Intematix Corporation, Fremont, CA (US)

( * ) Notice: Subject to any disclaimer, the term of this patent is extended or adjusted under 35 U.S.C. 154(b) by 0 days.

(21) Appl. No.: 16/903,251

(22) Filed: Jun. 16, 2020

(65) Prior Publication Data

US 2021/0013185 A1 Jan. 14, 2021

Related U.S. Application Data

(63) Continuation of application No. 16/517,524, filed on Jul. 19, 2019, now Pat. No. 10,685,941.

(Continued)

(51) Int. Cl.
*H01L 25/075* (2006.01)
*H01L 33/50* (2010.01)
(Continued)

(52) U.S. Cl.
CPC .......... *H01L 25/0753* (2013.01); *H01L 33/06* (2013.01); *H01L 33/08* (2013.01);
(Continued)

(58) Field of Classification Search
CPC ..... H01L 25/0753; H01L 33/06; H01L 33/08; H01L 33/32; H01L 33/507; H01L 33/504
See application file for complete search history.

(56) References Cited

U.S. PATENT DOCUMENTS 8,188,492 B2 ‡  5/2012  Lee ..................... H01L 25/0753
                                                              257/89
8,890,403 B2 ‡  11/2014 Sakuta .................. H05B 33/12
                                                              313/50
(Continued)

FOREIGN PATENT DOCUMENTS

CN      103383074 A   ‡  11/2013
CN      103383074 A      11/2013
(Continued)

OTHER PUBLICATIONS

Office Action, dated Dec. 2019; TW 108122226.‡
(Continued)

*Primary Examiner* — Joseph L Williams
(74) *Attorney, Agent, or Firm* — CrossPond Law

(57) ABSTRACT

A full spectrum white light emitting device includes photoluminescence materials which generate light with a peak emission wavelength in a range from about 490 nm to about 680 nm; and a broadband solid-state excitation source operable to generate broadband excitation light with a dominant wavelength in a range from about 420 nm to about 480 nm. The device is operable to generate white light with a Correlated Color Temperature in a range from about 1800K to about 6800K, a CRI R9 less than 90, a spectrum whose intensity decreases from its maximum value in the orange to red region of the spectrum to about 50% of the maximum value at a wavelength in a range from about 645 nm to about 695 nm, and over a wavelength range from about 430 nm to about 520 nm, a maximum percentage intensity deviation of light emitted by the device is less than 60% from the intensity of light of at least one of a blackbody curve and CIE Standard Illuminant D of the same Correlated Color Temperature.

15 Claims, 12 Drawing Sheets

SECTION A-A

Related U.S. Application Data

(60) Provisional application No. 62/872,227, filed on Jul. 9, 2019.

(51) Int. Cl.
  *H01L 33/08* (2010.01)
  *H01L 33/32* (2010.01)
  *H01L 33/06* (2010.01)

(52) U.S. Cl.
  CPC ............ *H01L 33/32* (2013.01); *H01L 33/507* (2013.01); *H01L 33/504* (2013.01)

(56) References Cited

U.S. PATENT DOCUMENTS

| | | | |
|---|---|---|---|
| 9,004,705 B2 ‡ | 4/2015 | Li | H01L 33/54 |
| | | | 362/84 |
| 9,590,149 B2 ‡ | 3/2017 | Lim | H01L 33/504 |
| 9,605,815 B2 ‡ | 3/2017 | Yamakawa | F21V 9/02 |
| 9,698,317 B2 ‡ | 7/2017 | Park | H01L 33/504 |
| 9,997,669 B2 ‡ | 6/2018 | Im | H01L 33/60 |
| 10,371,325 B1 ‡ | 8/2019 | Yuan | F21K 9/64 |
| 10,685,941 B1 | 6/2020 | Li et al. | |
| 2002/0117674 A1 ‡ | 8/2002 | Sugawara | H01L 33/08 |
| | | | 257/79 |
| 2005/0161690 A1 ‡ | 7/2005 | Lai | H01L 33/50 |
| | | | 257/98 |
| 2010/0289044 A1 | 11/2010 | Krames et al. | |
| 2013/0114242 A1 ‡ | 5/2013 | Pickard | F21V 7/30 |
| | | | 362/84 |
| 2014/0055982 A1 ‡ | 2/2014 | Tao | C09K 11/7733 |
| | | | 362/84 |
| 2018/0130928 A1 | 5/2018 | Vick et al. | |

FOREIGN PATENT DOCUMENTS

| | | | |
|---|---|---|---|
| JP | 2011192738 A | ‡ | 9/2011 |
| JP | 2011192738 A | | 9/2011 |
| JP | 2015126160 A | ‡ | 7/2015 |
| JP | 2015126160 A | | 7/2015 |
| TW | 201724553 A | ‡ | 7/2017 |
| TW | 201724553 A | | 7/2017 |
| WO | 2016039799 A1 | | 3/2016 |
| WO | 2017044380 A1 | | 3/2017 |
| WO | 2017131714 A1 | | 8/2017 |

OTHER PUBLICATIONS

Written Opinion PCT/IB2019/001003.‡
ISR PCT/IB2019/001003.‡
Cong Feng, Jian-an Huang and H. W. Choi "Monolithic Broadband InGaN Light-Emitting Diode", ACS Photonics 2016, 3, 7, ACS Publications, p. 1294-1300.‡
Rejection Decision, dated May 2020; TW 108122226.
U.S. Appl. No. 62/689,538.
U.S. Appl. No. 62/872,227.
U.S. Appl. No. 62/931,180.
ISR, Sep. 2020, PCT/US2020/040801.
Written Opinion, dated Sep. 2020, PCT/US2020/040801.
Zheng, Li-Li, et. al.; "Spectral Optimization of Three-Primary LEDs by Considering the Circadian Action Factor;" IEEE Photonics Journal, vol. 8, No. 6; Dec. 1, 2016; DOI 10.1109/JPHOT.2016.2623667.
International Search Report, dated Oct. 2020, PCT/US2020/040809.
Written Opinion, dated Oct. 2020, PCT/US2020/040089.
Zheng, Li-Li, et. al.; "Spectral optimization of Three-Primary LEDs by Considering the Circadian Action Factor," IEEE Photonics Journal, vol. 8, No. 6, Dec. 1, 2016.

‡ imported from a related application

SECTION A-A

SECTION B-B

FULL SPECTRUM WHITE LIGHT EMITTING DEVICES

CROSS REFERENCE TO RELATED APPLICATIONS

This application is a continuation of U.S. Utility application Ser. No. 16/517,524 filed Jul. 19, 2019, which in turn claims the benefit of priority to U.S. Provisional Application No. 62/872,277 filed Jul. 9, 2019, each of which is hereby incorporated by reference in its entirety.

FIELD OF THE INVENTION

Embodiments of the present invention are directed to full spectrum white light emitting devices comprising photoluminescence wavelength conversion materials. More particularly, although not exclusively, embodiments concern full spectrum white light emitting devices for generating full spectrum white light having a spectrum from blue light to red light that closely resembles natural sunlight.

BACKGROUND OF THE INVENTION

White light emitting LEDs ("white LEDs") include one or more photoluminescence materials (typically inorganic phosphor materials), which absorb a portion of the blue light emitted by the LED and re-emit visible light of a different color (wavelength). The portion of the blue light generated by the LED that is not absorbed by the phosphor material combined with the light emitted by the phosphor provides light which appears to the eye as being white in color. Due to their long operating life expectancy (>50,000 hours) and high efficacy (100 lumens per watt and higher), white LEDs are rapidly replacing conventional fluorescent, compact fluorescent and incandescent lamps.

Various metrics exist for quantifying the characteristics and quality of light generated by white lighting sources. The two most commonly used metrics within the solid-state lighting industry are, Correlated Color Temperature (CCT) and International Commission on Illumination (CIE) General Color Rendering Index (CRI) Ra.

The CCT of a lighting source is measured in kelvin (K) and is the color temperature of a Plankian (black-body) radiator that radiates light of a color that corresponds to the color of the light generated by the lighting source.

The General CRI Ra characterizes how faithfully a lighting source renders the true colors of an object and is based on a measure of how well a light source's illumination of eight color test samples (R1 to R8) compares with the illumination provided by a reference source. In general, the higher the value indicates its closeness to a black radiator and natural sunlight. General CRI Ra can take negative values and has a maximum value of 100. Since the color samples R1 to R8 are all pastel colors (low saturation colors "Light Grayish Red" to "Reddish Purple") the General CRI Ra gives a useful measure of subtle differences in light output of incandescent sources which generate a full spectrum that closely resembles sunlight. However, for white LEDs whose spectrum is composed of peaks, the General CRI Ra can prove to be inadequate as it is an average measure of color rendition over a limited range of colors and gives no information of the lighting source's performance for particular colors or highly saturated colors. Thus, when characterizing full spectrum solid-state white light emitting devices the CRI color samples R9 to R12 (saturated colors "Saturated Red", "Saturated Yellow", "Saturated Green", "Saturated Blue") and R13 to R15 ("Light Skin Tone", "Leaf Green", "Medium Skin Tone") should be considered to give a meaningful characterization of full spectrum light.

There is growing concern that artificial light disrupts the normal regulation of human physiology and psychology, such as hormone synthesis, sleep-wake cycle, and level of alertness. In particular, recent evidence indicates that high color temperature (5000K) and high Illuminance light, such as for example light generated by LEDs, suppress pre-sleep melatonin secretion as well as reduce subjective alertness. It has also been reported that blue light has a greater tendency than other colors to affect living organisms through the disruption of their biological processes which rely upon natural cycles (circadian) of daylight and darkness. It is believed that exposure to blue light late in the evening and at night can be detrimental to health.

Various metrics have been proposed for predicting the melatonin suppression effect. Two of the more common metrics for measuring circadian stimulus are (i) Circadian Action Factor (CAF) and (ii) Melanopic Response (MR). CAF and MR are the ratio of the circadian luminous efficacy of radiation (CER) to luminous efficacy of radiation (LER) and each provide a measure of the brains sensitivity to light, that is, a measure of human non-visual sensitivity to light. CAF is based on studies that measure human melatonin levels before and after exposure to specific wavelengths of light to establish a Circadian Action Spectrum (CAS). CAF, denoted $a_{cv}$, is the ratio of the circadian efficacy to luminous efficacy of radiation. MR is based on the absorption spectrum of the melanopsin photopigment found in mammalian ipRGCs (intrinsically photosensitive Retinal Ganglion Cells) to establish a melanopic response spectrum. MR is the ratio of the circadian efficacy to luminous efficacy of radiation. Recently, a new metric Equivalent Melanopic Lux (EML) has been proposed that is weighted to the spectral response of the ipRGCs.

Currently in the LED lighting industry, full spectrum LED devices seek to generate white light with a General CRI Ra equal to 100 such as is exhibited by incandescent lamps and black body radiation. Such LEDs, however, are found to sacrifice efficacy by 15 to 30% compared with white LEDs that generates light with a CRI Ra of about 80 (CRI80).

The present invention arose in an endeavor to overcome at least in part the shortcomings of known full spectrum LEDs and provide a full spectrum light emitting device with a efficacy at least approaching that of current CRI80 devices.

SUMMARY OF THE INVENTION

The invention concerns full spectrum white light emitting devices for generating full spectrum white light having a spectral content from blue light to red light that resembles natural sunlight as closely as possible. In particular, although not exclusively, embodiments of the invention are directed to ensuring that the full spectrum light resembles natural light in the blue to cyan region as closely as possible while optimizing (reducing) the deep red (e.g. corresponding to "Saturated Red"—CRI R9) of the spectrum to improve efficacy.

According to embodiments of the invention, full spectrum white light emitting devices generate full spectrum white light that closely resembles natural light in the blue to cyan (430 nm to 520 nm) region where human non-visual perception measured by Circadian Action Factor (CAF) is affected most. Full spectrum white light having such a spectral characteristic is believed to be beneficial to human wellbeing since this part of the spectral region impacts melatonin secretion which can influence the circadian cycle.

Full spectrum white light emitting devices in accordance with the invention utilize broadband solid-state excitation sources, for example blue LEDs, which generate broadband excitation light with a dominant wavelength in a range from about 420 nm to about 480 nm (that is in the blue region of the visible spectrum). In this patent specification "broadband" light is used to denote light that has a FWHM (Full Width Half Maximum) of at least 25 nm, preferably at least 30 nm; or may be used to denote blue light that is composed of a combination of at least two different wavelength blue light emissions in a wavelength range from about 420 nm to about 480 nm. Use of broadband blue excitation light enables the light emitting device to generate full spectrum light that closely resembles natural light in blue to cyan (420 nm to 520 nm) region of the spectrum.

According to an aspect of the present invention, there is envisaged a full spectrum white light emitting device comprising: photoluminescence materials which generate light with a peak emission wavelength in a range from about 490 nm to about 680 nm; and a broadband solid-state excitation source operable to generate broadband excitation light with a dominant wavelength in a range from about 420 nm to about 480 nm, wherein the device is operable to generate white light with a Correlated Color Temperature in a range from about 1800K to about 6800K, a CRI R9 less than 90, a spectrum whose intensity decreases from its maximum value in the orange to red region of the spectrum to about 50% of said maximum value at a wavelength in a range from about 645 nm to about 695 nm, and wherein, over a wavelength range from about 430 nm to about 520 nm, a maximum percentage intensity deviation of light emitted by the device is less than 60% from the intensity of light of at least one of a black-body curve and CIE Standard Illuminant D of the same Correlated Color Temperature. More particularly, the maximum intensity in the orange to red region of the spectrum corresponds to photoluminescence converted (generated) light and the maximum intensity occurs at a wavelength longer than about 570 nm. For instance, the maximum intensity may occur at wavelength ranging from about 590 nm to about 620 nm.

It may be that said maximum percentage intensity deviation of light emitted by the device is less than at least one of 50%, 40%, 30%, 20% and 10%.

The white light may have a Circadian Action Factor (CAF) that is within 5% of the black-body curve or CIE Standard Illuminant D.

In embodiments, the white light may have a CRI R8 that is less than 90.

It may be that the white light has a spectrum whose intensity decreases from its maximum value of light emitted by the device to about 50% of said maximum value at a wavelength that is from about 645 nm to about 665 nm, and has a CRI Ra greater than or equal to 80.

The white light may have a spectrum whose intensity decreases from its maximum value to about 50% of said maximum value of light emitted by the device at a wavelength that is from about 665 nm to about 690 nm, and has a CRI Ra greater than or equal to 90 and CRI R9 greater than 50.

In embodiments, the white light may have a spectrum whose intensity decreases from its maximum value to about 50% of said maximum value of light emitted by the device at a wavelength that is from about 680 nm to about 695 nm, and has a CRI Ra greater than or equal to 95 and a CRI R9 greater than 60.

It may be that the photoluminescence materials comprise at least one or a combination of photoluminescence materials which generates light with a peak emission wavelength from about 620 nm to about 655 nm.

The white light may have a Correlated Color Temperature from about 2700K to about 3000 K and the device may have an efficacy of at least 102 lm/W.

In embodiments, the white light may have a Correlated Color Temperature from about 4000K to about 6800 K and the device may have an efficacy of at least 110 lm/W.

It may be that the broadband solid-state excitation source generates broadband excitation light with a FWHM of at least 25 nm.

The broadband excitation light may comprise at least two blue light emissions.

In embodiments, the broadband solid-state excitation source may comprise: a first solid-state light source operable to generate a blue light emission with a first dominant wavelength in a range 420 nm to 480 nm; and a second solid-state light source operable to generate a different blue light emission with a second dominant wavelength in a range 420 nm to 480 nm.

It may be that the broadband solid-state excitation source comprises an LED having an active region with at least two different quantum wells that each generate a respective one of the at least two different wavelength blue light emissions.

In embodiments, the photoluminescence materials can comprise: a first photoluminescence material which generates light with a peak emission wavelength in a range 490 nm to 550 nm and a second photoluminescence material which generates light with a peak emission wavelength in a range 600 nm to 680 nm.

According to an aspect, the present invention encompasses a full spectrum white light emitting device comprising: photoluminescence materials which generate light with a peak emission wavelength in a range from about 490 nm to about 680 nm; and a broadband solid-state excitation source operable to generate broadband excitation light with a dominant wavelength in a range from about 420 nm to about 480 nm, wherein the device is operable to generate white light with a Correlated Color Temperature in a range from about 1800K and about 6800K and wherein the white light has a spectrum that has a CAF that is within 5% of at least one of the black-body curve and CIE Standard Illuminant D.

In embodiments, over a wavelength range from about 430 nm to about 520 nm, there may be a maximum percentage intensity deviation of light emitted by the device is less than 60% from the intensity of light of at least one of a black-body curve and CIE Standard Illuminant D of the same Correlated Color Temperature.

It may be that said maximum percentage intensity deviation of light emitted by the device less is than at least one of 50%, 40%, 30%, 20% and 10%.

The white light may have a spectrum whose intensity drops to half its maximum intensity at a wavelength that is from about 645 nm to about 695 nm.

In embodiments, the white light may have a CRI R9 less than 90.

It may be that the white light has a Correlated Color Temperature from about 2700K to about 3000 K and the device has an efficacy of at least 102 lm/W, or the white light has a Correlated Color Temperature from about 4000K to about 6800 K and the device has an efficacy of at least 110 lm/W.

Broadband excitation light can be generated using a combination of blue light emissions of two or more different wavelengths. The different wavelength blue light emissions can be generated in two ways: (i) using multiple individual blue LEDs (narrowband LEDs) of different dominant wavelengths or (ii) individual LEDs (broadband LEDs) that generate multiple blue wavelength emissions using, for example, specially designed multiple different quantum wells in the active region. Thus, a broadband solid-state excitation source can be constituted by one or more narrowband solid-state light sources; such as for example, LEDs or laser diodes, each of which "directly" generates narrowband blue light of different dominant wavelengths in a range from 420 nm to 480 nm. In embodiments, the broadband excitation light can comprise at least two blue light emissions. In some embodiments, there is a difference in wavelength between the at least two blue light emissions of at least 5 nm, or a difference in wavelength between the at least two blue light emissions of at least 10 nm. In some embodiments, the broadband solid-state excitation source comprises: a first solid-state light source operable to generate a blue light emission with a first dominant wavelength in a range 420 nm to 480 nm and a second solid-state light source operable to generate a different blue light emission with a second dominant wavelength in a range 420 nm to 480 nm. The first dominant wavelength can be in a range from 420 nm to 450 nm; and the second dominant wavelength can be in a range from 450 nm to 480 nm. The broadband blue excitation source may further comprise a third solid-state light source operable to generate a blue light emission with a third dominant wavelength in a range 420 nm to 480 nm which is different from the first and second dominant wavelengths.

Alternatively, a broadband solid-state excitation source also encompasses a broadband solid-state light source; for example, a broadband blue LED such as an InGaN/GaN blue LED having an active region that directly generates blue light emissions of multiple different wavelengths using different quantum wells in a multiple-quantum-well (MQW) structure. Broadband solid-state excitation sources of the invention are to be contrasted with known white LEDs that utilize narrowband blue LEDs that generate blue light of a single narrowband wavelength having a FWHM in a range 15 nm to 20 nm. Broadband blue solid-state excitation sources of the invention are to be further contrasted with known white LEDs that utilize UV solid-state light sources (UV LEDs) in which the blue excitation light is generated indirectly through a process of photoluminescence conversion of UV light using a blue light emitting (420 nm to 480 nm) photoluminescence material (phosphor). In other words, broadband solid-state excitation sources/white light emitting devices in accordance with the invention do not utilize/include a photoluminescence material to generate excitation light in a range 420 nm to 480 nm.

In some embodiments, the broadband solid-state excitation source comprises an LED having an active region with at least two different quantum wells that each generate a respective one of the at least two different wavelength blue light emissions.

Embodiments of the invention find utility in a packaged device where the photoluminescence materials (e.g. yellow to green and orange to red photoluminescence materials) are packaged with the broadband solid-state excitation source. In other embodiments, the photoluminescence materials can be located remote to the broadband solid-state excitation source.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

(dotted line), and (iii) Plankian spectrum (dashed line) for a CCT of 5000K that is nominally the same as Dev.7 and Com.5.

DETAILED DESCRIPTION OF THE INVENTION

Figure 1A:
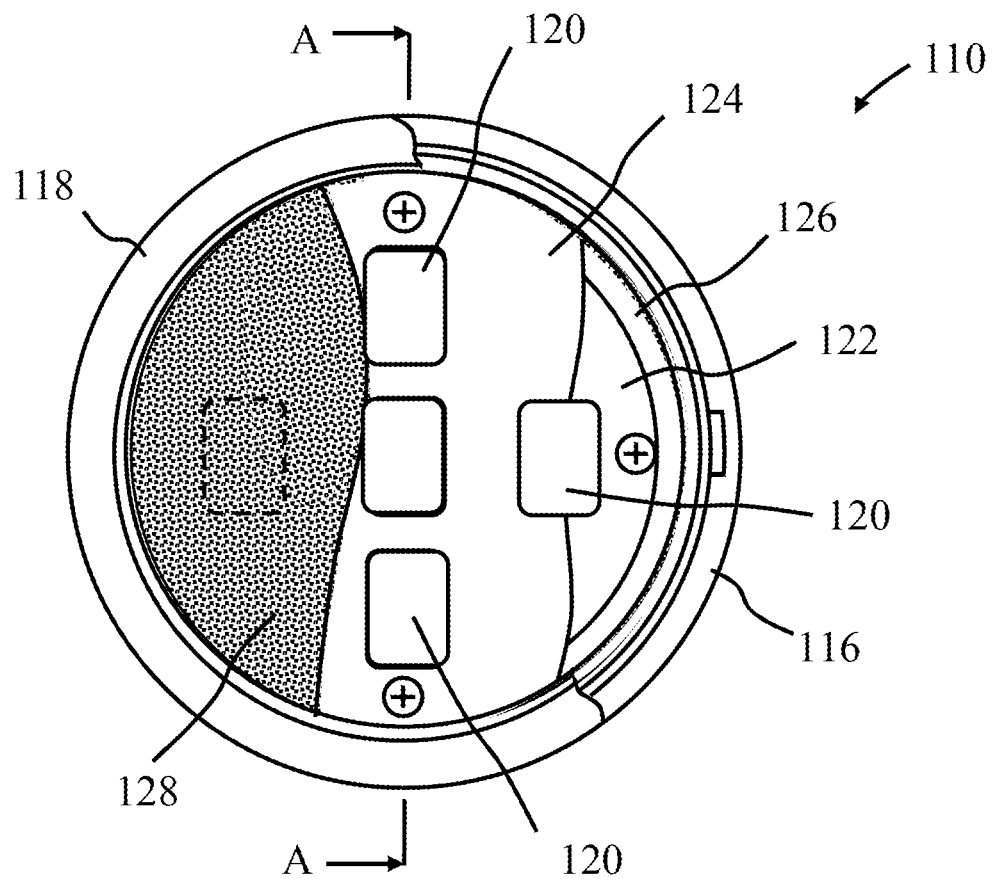
FIGS. 1a and 1b show a remote phosphor full spectrum white light emitting device, according to some embodiments.

Embodiments of the present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

Throughout this specification, like reference numerals preceded by the figure number are used to denote like features.

Embodiments of the invention concern white light emitting devices that comprise a broadband solid-state excitation source, for example one or more LEDs, that is operable to generate broadband blue excitation light with a dominant wavelength in a range from 420 nm to 480 nm. In this patent specification "broadband" blue light is used to denote blue light that has a FWHM (Full Width Half Maximum) at least 25 nm, preferably at least 30 nm; or may be used to denote blue light that is composed of a combination of at least two different wavelength blue light emissions in a wavelength range 420 nm to 480 nm. More particularly, although not exclusively, embodiments of the invention concern white light emitting devices for generating full spectrum white light that closely resembles natural light in the blue to cyan region of the visible spectrum (about 430 nm to about 520 nm).

Remote Phosphor Full Spectrum White Light Emitting Devices

Figure 1B:
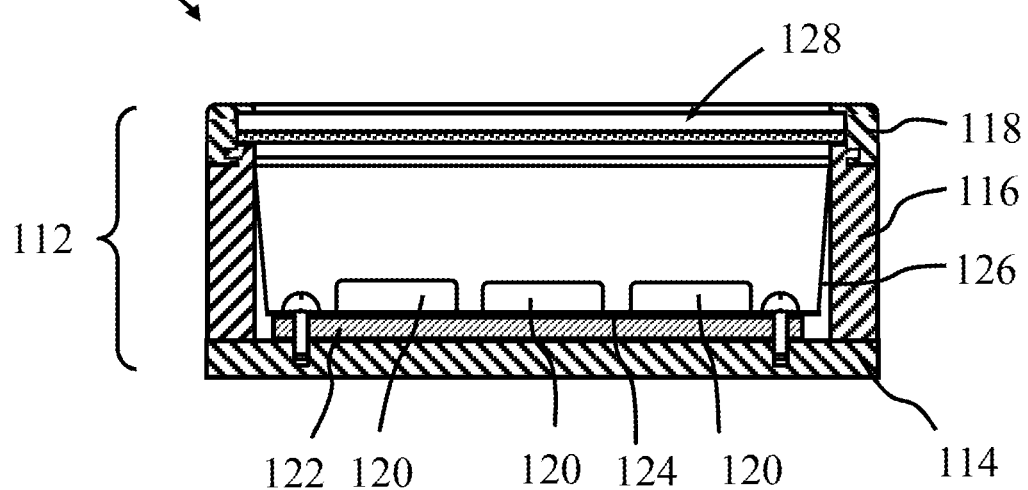

FIGS. 1a and 1b illustrate a remote phosphor solid-state full spectrum white light emitting device according to an embodiment of the invention in which FIG. 1a is a partial cross-sectional plan view and FIG. 1b is a sectional view through A-A. The device 110 is configured to generate full spectrum white light with a CCT (Correlated Color Temperature) of between 1800K and 6800K. The device can be used alone or comprise a part of a downlight or other lighting arrangement. The device 110 comprises a hollow cylindrical body 112 composed of a circular disc-shaped base 114, a hollow cylindrical wall portion 116 and a detachable annular top 118. To aid in the dissipation of heat, the base 114 is preferably fabricated from aluminum, an alloy of aluminum or any material with a high thermal conductivity. The base 114 can be attached to the wall portion 116 by screws or bolts or by other fasteners or by means of an adhesive.

The device 110 further comprises a plurality (five in the example of FIGS. 1a and 1b) of broadband blue solid-state excitation sources 120 that are mounted in thermal communication with a circular-shaped MCPCB (metal core printed circuit board) 122. Various embodiments of the broadband blue solid-state excitation sources 120 are illustrated in FIGS. 2a to 4b. To maximize the emission of light, the device 10 can further comprise light reflective surfaces 124 and 126 that respectively cover the face of the MCPCB 122 and the inner curved surface of the cylindrical wall 116.

The device 110 further comprises a photoluminescence wavelength conversion component 128 that is located remotely to the excitation sources 120 and operable to absorb a portion of the excitation light generated by the excitation sources 120 and convert it to light of a different wavelength by a process of photoluminescence. The emission product of the device 110 comprises the combined light generated by the broadband blue excitation sources 120 and photoluminescence light generated by the photoluminescence wavelength conversion component 128. The photoluminescence wavelength conversion component may be formed of a light transmissive material (for example, polycarbonate, acrylic material, silicone material, etc.) that incorporates a mixture of a yellow, red and/or green phosphor. Furthermore, in embodiments, the photoluminescence wavelength conversion component may be formed of a light transmissive substrate that is coated with phosphor material(s). The wavelength conversion component 128 is positioned remotely to the excitation sources 120 and is spatially separated from the excitation sources. In this patent specification, "remotely" and "remote" means in a spaced or separated relationship. Typically, wavelength conversion component and excitation sources are separated by an air, while in other embodiments they can be separated by a suitable light transmissive medium, such as for example a light transmissive silicone or epoxy material. The wavelength conversion component 128 is configured to completely cover the housing opening such that all light emitted by the lamp passes through the wavelength component 128. As shown, the wavelength conversion component 128 can be detachably mounted to the top of the wall portion 116 using the top 118 enabling the component and emission color of the lamp to be readily changed.

Figure 2A:
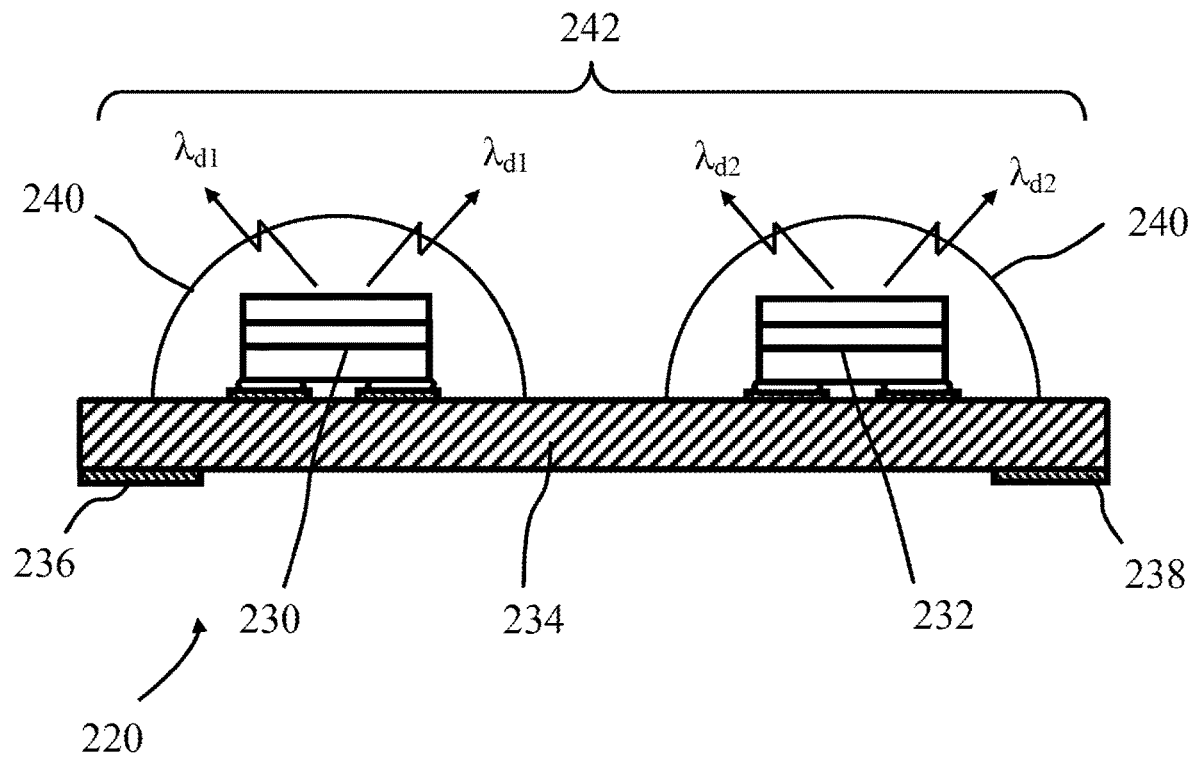
FIG. 2a is a schematic of a broadband blue solid-state excitation source in accordance with an embodiment of the invention for use in the full spectrum white light emitting device of FIGS. 1a and 1b.

FIG. 2a is a schematic representation of a broadband blue solid-state excitation source 220, according to an embodiment of the invention. The broadband blue solid-state excitation source 220 is configured to generate broadband blue excitation light with a dominant wavelength in a range 420 nm to 470 nm, that is, in the blue region of the visible spectrum. In this embodiment, it also has a FWHM in a range 25 nm to 50 nm. In accordance with an embodiment of the invention, the broadband blue solid-state excitation source 220 comprises a first solid-state light source 230 and a second solid-state light source 232, which in this example are narrowband blue LED chips (e.g. blue-emitting GaN -based LED chips). The first solid-state light source 230 generates a blue light emission having a first dominant wavelength $\lambda_{d1}$ in a range from 420 nm to 470 nm and the second solid-state light source 232 generates a blue light emission having a second dominant wavelength $\lambda_{d2}$ in a range from 420 nm to 470 nm. The first and second solid-state light sources are selected such that the dominant wavelengths of light generated by the sources are different (i.e. $\lambda_{d1}$ is different to $\lambda_{d2}$). The combination of light from the first and second solid-state light sources 230/232 constitutes the broadband blue excitation light output 242 of the broadband blue solid-state excitation source 220 and has a dominant wavelength in a range 420 nm to 470 nm and has a FWHM in a range 25 nm to 50 nm. It will be understood that in other embodiments the solid-state excitation source may comprise a single solid-state light source. In this specification, a single solid-state light source is defined as one or more solid-state light sources each of which generates light with the same (i.e. single/solitary) dominant wavelength and with a FWHM of at least 25 nm.

As indicated in FIG. 2a, the broadband blue solid-state excitation source 220 can comprise a surface mountable device (SMD), such as for example an SMD 2835 LED package, in which the first and second solid-state light sources are flip-chip bonded on a top face of a substrate 234. Electrical contacts 236, 238 can be provided on the bottom face of the substrate 234 for operating the excitation source. The first and second solid-state light sources 230, 232 can be encapsulated with a light transmissive optical encapsulant 240, such as for example a silicone or epoxy material.

Figure 2B:
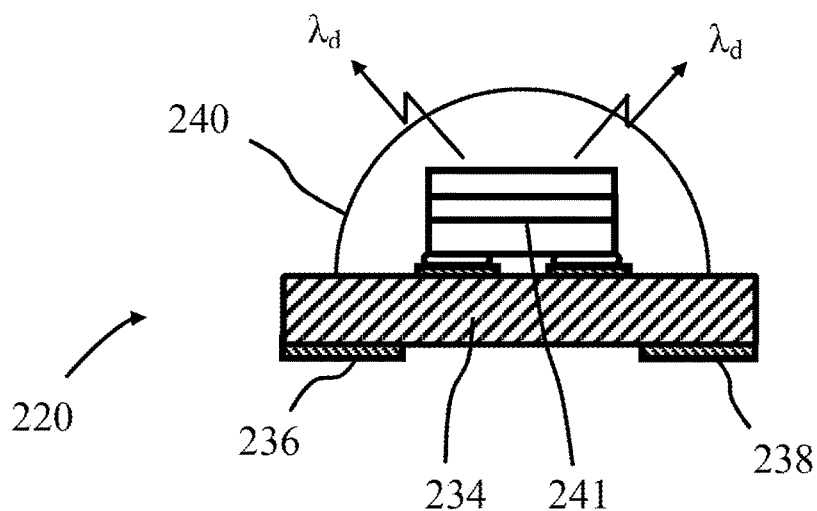
FIG. 2b is a schematic of a broadband blue solid-state excitation source in accordance with an another embodiment of the invention for use in the full spectrum white light emitting device of FIGS. 1a and 1b.

FIG. 2b is a schematic representation of a broadband blue solid-state excitation source 220, according to an embodiment of the invention. The solid-state excitation source 220 is configured to generate excitation light with a dominant wavelength in a range 420 nm to 470 nm, that is, in the blue region of the visible spectrum. In this embodiment, it also has a FWHM in a range 25 nm to 50 nm. In accordance with an embodiment of the invention, the solid-state excitation source 220 comprises a broadband solid-state light source 241, which in this example is a single broadband LED such as for example an InGaN/GaN blue LED having an active region with multiple-quantum-wells (MQWs), as disclosed in Appl. Phys. lett. 75, 1494 (1999) Tran C A et al. entitled "Growth of InGaN multiple-quantum-well blue light-emitting diodes on silicone by metal organic vapor phase epitaxy". The broadband solid-state light source 241 generates broadband blue light comprising multiple overlapping blue light emissions of peak wavelengths in a range from 420 nm to 470 nm. Thus, the single solid-state light source 241 generates light with a single/solitary dominant wavelength and with a FWHM of at least 25 nm.

As indicated in FIG. 2b, the solid-state excitation source 220 can comprise a surface mountable device (SMD), such as for example an SMD 2835 LED package, in which the solid-state light source is flip-chip bonded on a top face of a substrate 234. Electrical contacts 236, 238 can be provided on the bottom face of the substrate 234 for operating the excitation source. The solid-state light source 241 can be encapsulated with a light transmissive optical encapsulant 240, such as for example a silicone or epoxy material.

Packaged Full Spectrum White Light Emitting Devices

Figure 3A:
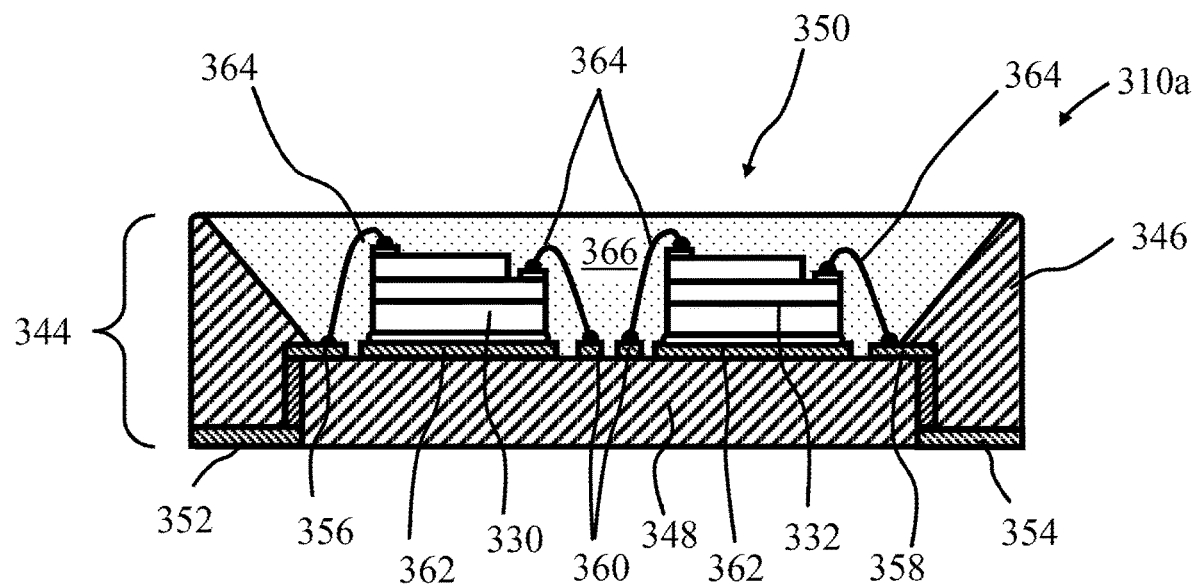
FIG. 3a is a schematic cross-sectional view of a full spectrum white light emitting device, according to some embodiments.

FIG. 3a is a schematic cross-sectional representation of a packaged full spectrum white light emitting device 310a, according to an embodiment of the invention. The device 310a is configured to generate full spectrum white light with a CCT (Correlated Color Temperature) of in a range 1800 K to 6800K.

In accordance with embodiments of the invention, the device 310a comprises a broadband blue solid-state excitation source constituted by first and second solid-state light sources 330, 332, for example blue-emitting GaN (gallium nitride)-based LED chips, that are housed within a package 344. In a similar/same manner as described above, the first solid-state light source 330 can generate a blue light emission having a first dominant wavelength $\lambda_{d1}$ in a range from 420 nm to 470 nm and the second solid-state light source 332 can generate a blue light emission having a second dominant wavelength $\lambda_{d2}$ in a range from 420 nm to 470 nm. The dominant wavelength $\lambda_{d1}$ of the first solid-state light source is different from the dominant wavelength $\lambda_{d2}$ of the second solid-state light source. The package, which can for example comprise Surface Mountable Device (SMD) such as an SMD 2835 LED package, comprising upper portion 346 and base portion 348. The upper body part 346 defines a recess 350 which is configured to receive the solid-state light sources 330, 332. The package 344 can further comprise electrical connectors 352 and 354 on an exterior face of the base of the package 344. The electrical connectors 352, 354 can be electrically connected to electrode contact pads 356, 358 and 360 on the floor of the recess 350. Using adhesive or solder, the solid-state light sources (LED chips) 330, 332 can be mounted to a thermally conductive pad 362 located on the floor of the recess 350. The LED chip's electrode pads can be electrically connected to corresponding electrode contact pads 356, 358 and 360 on the floor of the package 344 using bond wires 362. Alternatively, the LED chips can be flip-chip mounted in and electrically connected to the package. The recess 350 is filled with a light transmissive optical encapsulant 364, typically an optically clear silicone, which is loaded with a mixture of photoluminescence materials such that the exposed surfaces of the LED chips 330, 332 are covered by the photoluminescence/silicone material mixture. To enhance the emission brightness of the device the walls of the recess 350 can be inclined and have a light reflective surface. Of course, it will be understood that in other embodiments the one or more solid-state light sources (LED chips 330, 332) each generate light with the same (i.e. single/solitary) dominant wavelength and with a FWHM of at least 25 nm.

Figure 3B:
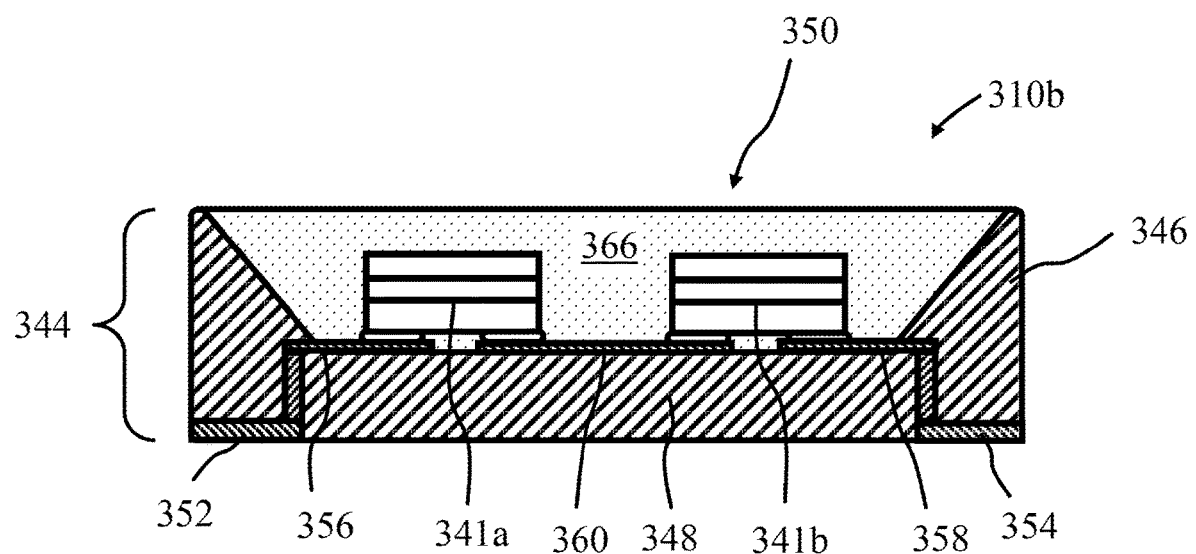
FIG. 3b is a schematic cross-sectional view of a full spectrum white light emitting device, according to some embodiments.

FIG. 3b is another embodiment of the present invention. It is similar to FIG. 3a except that the first and second narrowband solid-state light sources are replaced by two broadband blue LEDs 341a/341b having an active region with multiple-quantum-wells. Typically, the first and second broadband blue solid-state light sources 341a/341b each generate broadband blue excitation light having dominant wavelengths $\lambda_d$ which are the same.

Figure 4A:
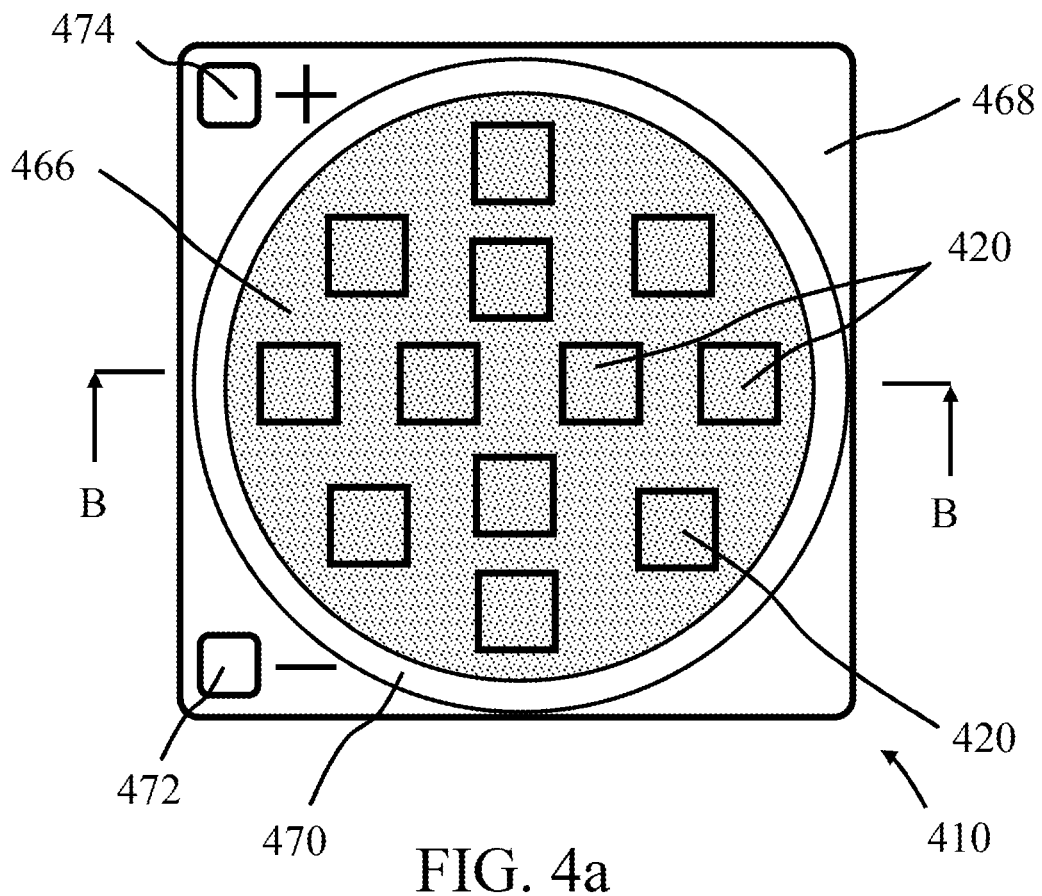
FIGS. 4a and 4b is a schematic of a full spectrum white light emitting device, according to some embodiments.
Figure 4B:
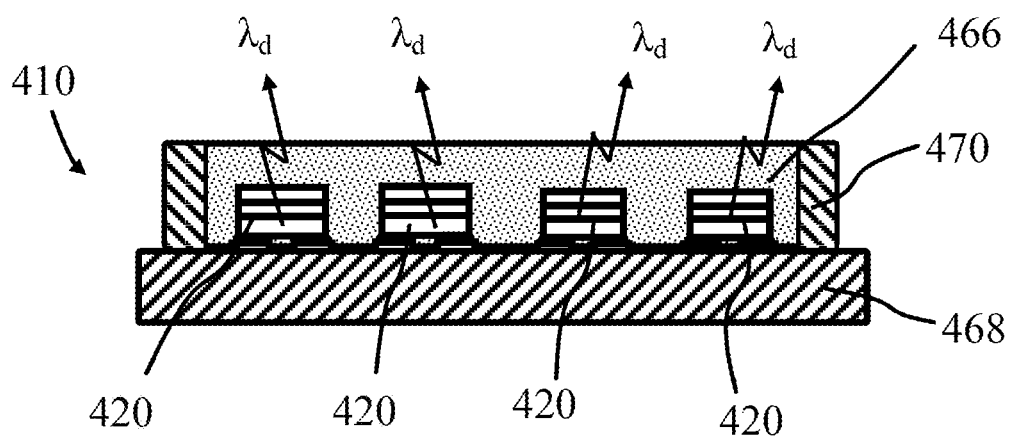

FIGS. 4a and 4b illustrate a Chip On Board (COB) packaged full spectrum white light emitting device 410 according to an embodiment of the invention in which FIG. 4a is a plan view and FIG. 4b is a sectional view through B-B. The device 410 is configured to generate warm white light with a CCT (Correlated Color Temperature) of between 2500K and 5000K and a CRI (Color Rendering Index) of greater than 95.

The device 410 comprises a plurality (twelve in the example of FIG. 4a) broadband blue solid-state excitation sources 420, for example broadband blue-emitting GaN (gallium nitride)-based LED flip-chip dies, mounted in thermal communication with a square-shaped MCPCB 468.

As indicated in FIG. 4a, the excitation sources 420 can be configured as a generally circular array. The solid-state excitation sources (broadband LED dies) 420 can each generate excitation light having a dominant wavelength $\lambda_d$ in a range from 440 nm to 455 nm. In this embodiment, they have a FWHM (Full Width Half Maximum) in a range 25 nm to 50 nm. Electrical contacts 472, 474 can be provided on the top face of the MCPCB 468 for operating the white light emitting device 410. As shown, the broadband LED flip-chip dies 420 are encapsulated with a light transmissive optical encapsulant 466, such as for example a silicone or epoxy material, which is loaded with a mixture of photoluminescence materials such that the exposed surfaces of the LED dies 420 are covered by the photoluminescence/silicone material mixture. As shown, the light transmissive encapsulant/photoluminescence material mixture 466 can be contained within an annular-shaped wall 470. Of course, it will be understood that in other embodiments, the arrangement depicted in FIGS. 4a and 4b could comprise solid-state excitation sources 420 constituted by two or more LEDs rather than a single broadband InGaN/GaN blue LED having an active region with multiple-quantum-wells.

Green to Yellow Photoluminescence Materials

In this patent specification, a green to yellow photoluminescence material refers to a material which generates light having a peak emission wavelength ($\lambda_{pe}$) in a range ~490 nm to ~570 nm, that is in the green to yellow region of the visible spectrum. Preferably, the green to yellow photoluminescence material has a broad emission characteristic and preferably has a FWHM (Full Width Half Maximum) of ~100 nm or wider. The green to yellow photoluminescence material can comprise any photoluminescence material, such as for example, garnet-based inorganic phosphor materials, silicate phosphor materials and oxynitride phosphor materials. Examples of suitable green to yellow phosphors are given in Table 1.

In some embodiments, the green to yellow photoluminescence materials comprises a cerium-activated yttrium aluminum garnet phosphor of general composition $Y_3(Al,Ga)_5O_{12}$:Ce (YAG) such as for example a YAG series phosphor from Intematix Corporation, Fremont Calif., USA which have a peak emission wavelength of in a range 527 nm to 543 nm and a FWHM of ~120 nm. In this patent specification, the notation YAG # represents the phosphor type—YAG—based phosphors—followed by the peak emission wavelength in nanometers (#). For example, YAG535 denotes a YAG phosphor with a peak emission wavelength of 535 nm. The green to yellow photoluminescence material may comprise a cerium-activated yttrium aluminum garnet phosphor of general composition $(Y,Ba)_3(Al,Ga)_5O_{12}$:Ce (YAG) such as for example a GNYAG series phosphor from Intematix Corporation, Fremont Calif., USA. In some embodiments, the green photoluminescence material can comprise an aluminate (LuAG) phosphor of general composition $Lu_3Al_5O_{12}$:Ce (GAL). Examples of such phosphors include for example the GAL series of phosphor from Intematix Corporation, Fremont Calif., USA which have a peak emission wavelength of 516 nm to 560 nm and a FWHM of ~120 nm. In this patent specification, the notation GAL # represents the phosphor type (GAL)—LuAG—based phosphors—followed by the peak emission wavelength in nanometers (#). For example, GAL520 denotes a GAL phosphor with a peak emission wavelength of 520 nm.

Examples of green to yellow silicate phosphors include europium activated ortho-silicate phosphors of general composition $(Ba, Sr)_2SiO_4$:Eu such as for example G, EG, Y and EY series of phosphors from Intematix Corporation, Fremont Calif., USA which have a peak emission wavelength in a range 507 nm to 570 nm and a FWHM of ~70 nm to ~80 nm.

In some embodiments, the green to yellow phosphor can comprise a green-emitting oxynitride phosphor as taught in U.S. Pat. No. 8,679,367 entitled "Green-Emitting (Oxy) Nitride-Based Phosphors and Light Emitting Devices Using the Same" which is hereby incorporated in its entirety. Such a green-emitting oxynitride (ON) phosphor can have a general composition $Eu^{2+}:M^{2+}Si_4AlO_xN_{(7-2x/3)}$ where $0.1 \leq x \leq 1.0$ and $M^{2+}$ is one or more divalent metal selected from the group consisting of Mg, Ca, Sr, Ba, and Zn. In this patent specification, the notation ON # represents the phosphor type (oxynitride) followed by the peak emission wavelength ($\lambda_{pe}$) in nanometers (#). For example ON495 denotes a green oxynitride phosphor with a peak emission wavelength of 495 nm.

TABLE 1

Example green to yellow photoluminescence materials

| Phosphor | General Composition | | Wavelength $\lambda_{pe}$ (nm) |
|---|---|---|---|
| YAG (YAG #) | $Y_{3-x}(Al_{1-y}Ga_y)_5O_{12}$:Ce$_x$ | $0.01 < x < 0.2$ & $0 < y < 2.5$ | 520-570 |
| GNYAG (YAG #) | $(Y,Ba)_{3-x}(Al_{1-y}Ga_y)_5O_{12}$:Ce$_x$ | $0.01 < x < 0.2$ & $0 < y < 2.5$ | 520-550 |
| LuAG (GAL #) | $Lu_{3-x}(Al_{1-y}M_y)_5O_{12}$:Ce$_x$ | $0.01 < x < 0.2$ & $0 < y < 1.5$ M = Mg, Ca, Sr, Ba, Ga, | 500-550 |
| LuAG (GAL #) | $Lu_{3-x}(Al_{1-y}Ga_y)_5O_{12}$:Ce$_x$ | $0.01 < x < 0.2$ & $0 < y < 1.5$ | 500-550 |
| Silicate | $A_2SiO_4$:Eu | A = Mg, Ca, Sr, Ba | 500-575 |
| Silicate | $(Sr_{1-x}Ba_x)_2SiO_4$:Eu | $0.3 < x < 0.9$ | 500-575 |

Orange to Red Photoluminescence Materials

The orange to red photoluminescence material can comprise any orange to red photoluminescence material, typically a phosphor, that is excitable by blue light and operable to emit light with a peak emission wavelength $\lambda_{pe}$ in a range about 600 nm to about 670 nm and can include, for example, a europium activated silicon nitride-based phosphor, α-SiAlON, Group IIA/IIB selenide sulfide-based phosphor or silicate-based phosphors. Examples of orange to red phosphors are given in Table 2.

In some embodiments, the europium activated silicon nitride-based phosphor comprises a Calcium Aluminum Silicon Nitride phosphor (CASN) of general formula $CaAlSiN_3:Eu^{2+}$. The CASN phosphor can be doped with other elements such as strontium (Sr), general formula $(Sr,Ca)AlSiN_3:Eu^{2+}$. In this patent specification, the notation CASN # represents the phosphor type (CASN) followed by the peak emission wavelength ($\lambda_{pe}$) in nanometers (#). For example CASN615 denotes an orange to red CASN phosphor with a peak emission wavelength of 615 nm.

In one embodiment, the orange to red phosphor can comprise an orange to red-emitting phosphor as taught in U.S. Pat. No. 8,597,545 entitled "Red-Emitting Nitride- Based Calcium-Stabilized Phosphors" which is hereby incorporated in its entirety. Such a red emitting phosphor comprises a nitride-based composition represented by the chemical formula $M_aSr_bSi_cAl_dN_eEu_f$ wherein: M is Ca, and $0.1 \leq a \leq 0.4$; $1.5 < b < 2.5$; $4.0 \leq c \leq 5.0$; $0.1 \leq d \leq 0.15$; $7.5 < e < 8.5$; and $0 < f < 0.1$; wherein $a+b+f > 2+d/v$ and v is the valence of M.

Alternatively, the orange to red phosphor can comprise an orange to red emitting nitride-based phosphor as taught in U.S. Pat. No. 8,663,502 entitled "Red-Emitting Nitride-Based Phosphors" which is hereby incorporated in its entirety. Such a red emitting phosphor comprising a nitride-based composition represented by the chemical formula $M_{(x/v)}M'_2Si_{5-x}Al_xN_8$:RE, wherein: M is at least one monovalent, divalent or trivalent metal with valence v; M' is at least one of Mg, Ca, Sr, Ba, and Zn; and RE is at least one of Eu, Ce, Tb, Pr, and Mn; wherein x satisfies $0.1 \leq x < 0.4$, and wherein said red-emitting phosphor has the general crystalline structure of $M'_2Si_5N_8$:RE, Al substitutes for Si within said general crystalline structure, and M is located within said general crystalline structure substantially at the interstitial sites. An example of one such a phosphor is XR610 red nitride phosphor from Intematix Corporation, Fremont Calif., USA which has a peak emission wavelength of 610 nm.

Orange to red phosphors can also include Group IIA/BB selenide sulfide-based phosphors. A first example of a Group IIA/IIB selenide sulfide-based phosphor material has a composition $MSe_{1-x}S_x$:Eu, wherein M is at least one of Mg, Ca, Sr, Ba and Zn and $0 < x < 1.0$. A particular example of this phosphor material is CSS phosphor ($CaSe_{1-x}S_x$:Eu). Details of CSS phosphors are provided in co-pending United States patent application Publication Number US2017/0145309 filed 30 Sep. 2016, which is hereby incorporated by reference in its entirety. The CSS orange to red phosphors described in United States patent publication US2017/0145309 can be used in the present invention. The emission peak wavelength of the CSS phosphor can be tuned from 600 nm to 650 nm by altering the S/Se ratio in the composition and exhibits a narrow-band red emission spectrum with FWHM in the range ~48 nm to ~60 nm (longer peak emission wavelength typically has a larger FWHM value). In this patent specification, the notation CSS # represents the phosphor type (CSS) followed by the peak emission wavelength in nanometers (#). For example CSS615 denotes a CSS phosphor with a peak emission wavelength of 615 nm. To improve reliability, the CSS phosphor particles can be coated with one or more oxides, for example: aluminum oxide ($Al_2O_3$), silicon oxide ($SiO_2$), titanium oxide ($TiO_2$), zinc oxide (ZnO), magnesium oxide (MgO), zirconium oxide ($ZrO_2$), boron oxide ($B_2O_3$) or chromium oxide (CrO). Alternatively and/or in addition, the narrow-band red phosphor particles may be coated with one or more fluorides, for example: calcium fluoride ($CaF_2$), magnesium fluoride ($MgF_2$), zinc fluoride ($ZnF_2$), aluminum fluoride ($AlF_3$) or titanium fluoride ($TiF_4$). The coatings may be a single layer, or multiple layers with combinations of the aforesaid coatings. The combination coatings may be coatings with an abrupt transition between the first and second materials, or may be coatings in which there is a gradual/smooth transition from the first material to the second material thus forming a zone with mixed composition that varies through the thickness of the coating.

In some embodiments, the orange to red phosphor can comprise an orange-emitting silicate-based phosphor as taught in U.S. Pat. No. 7,655,156 entitled "Silicate-Based Orange Phosphors" which is hereby incorporated in its entirety. Such an orange-emitting silicate-based phosphor can have a general composition $(Sr_{1-x}M_x)_yEu_zSiO_5$ where $0 < x \leq 0.5$, $2.6 \leq y \leq 3.3$, $0.001 \leq z \leq 0.5$ and M is one or more divalent metal selected from the group consisting of Ba, Mg, Ca, and Zn. In this patent specification, the notation O # represents the phosphor type (orange silicate) followed by the peak emission wavelength ($\lambda_{pe}$) in nanometers (#). For example, O600 denotes an orange silicate phosphor with a peak emission wavelength of 600 nm.

TABLE 2

Example orange to red photoluminescence materials

| Phosphor | General Composition | | Wavelength $\lambda_{pe}$ (nm) |
|---|---|---|---|
| CASN (CASN #) | $(Ca_{1-x}Sr_x)AlSiN_3$:Eu | $0.5 < x \leq 1$ | 600–660 |
| 258 nitride Group IIA/IIB | $Ba_{2-x}Sr_xSi_5N_8$:Eu | $0 \leq x \leq 2$ M = Mg, Ca, Sr, Ba, Zn | 580–630 |
| Selenide Sulfide (CSS #) | $MSe_{1-x}S_x$:Eu | $0 < x < 1.0$ | 600–650 |
| CSS (CSS #) | $CaSe_{1-x}S_x$:Eu | $0 < x < 1.0$ | 600–650 |
| Silicate (O #) | $(Sr_{1-x}M_x)_yEu_zSiO_5$ | M = Ba, Mg, Ca, Zn $0 < x \leq 0.5$ $2.6 \leq y \leq 3.3$ $0.001 \leq z \leq 0.5$ | 565–610 |

1800K to 6800K Full Spectrum White Light Emitting Devices

As described above, embodiments of the invention concern full spectrum white light emitting devices that generate full spectrum light that closely resembles natural light, in particular although not exclusively, in the in blue to cyan (430 nm to 520 nm) region of the visible spectrum where human non-visual perception, as for example, measured by CAF (Circadian Action Factor) are affected most. According to other aspects, the invention concerns improving the efficacy of full spectrum white light emitting devices while maintaining the spectrum close to the natural light in the wavelength ranging from about 430 nm to about 520 nm. The inventors have discovered that the efficacy of full spectrum white light emitting device can be improved by optimizing (reducing) the energy content in the red region of the spectrum, in particular the energy content corresponding to the "Saturated Red"—CRI R9 and "Reddish Purple"—CRI R8 while maintaining the spectral content corresponding to the blue and cyan regions (430 nm to 520 nm) to closely resemble natural light. Such an improvement in efficacy can be achieved by configuring the device such that it generates full spectrum white light having a spectrum with an intensity roll-off (tail) in the orange to red region of the visible spectrum that decreases (drops) to half its maximum intensity in a wavelength range from about 645 nm to about 695 nm).

Figure 5:
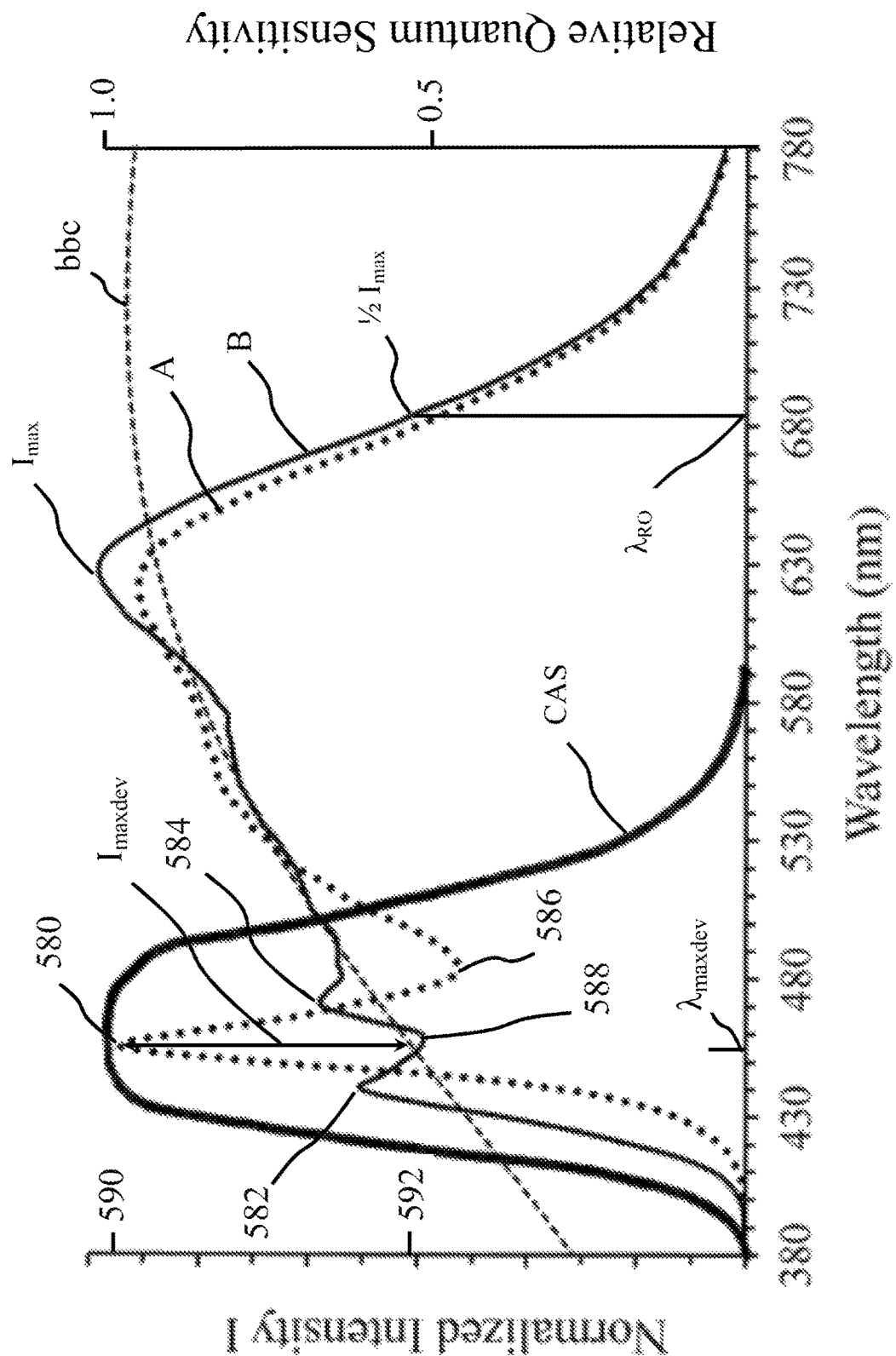
FIG. 5 are spectra, normalized intensity I versus wavelength (nm), for (i) a spectrum denoted A (dotted line) for a known full spectrum light emitting device that utilizes a narrowband excitation source, (ii) a spectrum denoted B (thin solid line) for a full spectrum light emitting device in accordance with the invention that utilizes a broadband excitation source (iii) black-body curve (bbc) (dashed line) for a CCT that is nominally the same as that of spectra A and B, and (iv) the Circadian Action Spectrum (CAS)—thick solid line, Relative Quantum Sensitivity versus wavelength (nm)

FIG. 5 are spectra, normalized intensity I versus wavelength (nm) for (i) a spectrum denoted A (dotted line) for a known full spectrum light emitting device that utilizes a narrowband excitation source, (ii) a spectrum denoted B (thin solid line) for a full spectrum light emitting device in accordance with the invention that utilizes a broadband excitation source (iii) black-body curve (bbc) (dashed line) for a CCT that is nominally the same as that of spectra A and B, and (iv) the Circadian Action Spectrum (CAS)—thick solid line, Relative Quantum Sensitivity versus wavelength (nm). The figure defines various parameters used in the patent specification and illustrates the principle of the invention.

Referring to FIG. 5, the Circadian Action Spectrum (CAS), also referred to as spectral circadian efficiency function c(λ), represents human non-visual relative sensitivity to light. The maximum sensitivity of c(λ) occurs at a wavelength of 460 nm. The CAS suggests that the 430 nm to 520 nm portion of the spectrum as being the most significant wavelengths for providing circadian input for regulating melatonin secretion.

Visually comparing the spectrum A with the back-body curve (bbc), it will be noted that spectrum A exhibits a peak 580, corresponding to the excitation light generated by the narrowband excitation source, whose intensity deviates significantly from that of the bbc (i.e. peak intensity is very much higher than that of the bbc at the same wavelength). In comparison, spectrum B exhibits two peaks 582, 584, corresponding to the excitation light generated by the broadband excitation source whose intensity, compared with spectrum A, deviates only slightly from that of the bbc (i.e. the peak intensities are slightly higher than the bbc at the same wavelengths). It is to be further noted that the peak 580 occurs at a wavelength of 455 nm that is close to the maximum sensitivity of the CAS which is at a wavelength of 460 nm. Moreover, it is to be noted that spectrum A exhibits a trough (valley) 586 whose minimum intensity deviates significantly from that of the bbc (i.e. the trough intensity is much lower than the bbc). In comparison, spectrum B exhibits a trough (valley) 588 that whose minimum intensity, compared with spectrum A, deviates only slightly from that of the bbc (i.e. the trough intensity is slight lower than the bbc). As can be seen from the figure, the smaller deviation of emission peaks 582 and 584 of spectrum B (compared with peak 584 of spectrum A) and the smaller deviation of trough 588 of spectrum B (compared with trough 586 of spectrum A) from the bbc indicates that spectrum B more closely resembles the bbc (Plankian spectrum) over a wavelength range 430 nm to 520 nm (blue to cyan). It will be further appreciated that spectrum B more closely resembles natural light over this wavelength region where human non-visual perception measured by CAF (Circadian Action Factor) are affected most and this can be beneficial to human wellbeing.

A metric for quantifying how closely the spectrum resembles the bbc is a maximum (largest) percentage intensity deviation ($I_{maxdev}$) from the intensity of light of the bbc of the same Correlated Color Temperature. That is, over a wavelength range from about 430 nm to 520 nm, $I_{maxdev}$ is the maximum (largest) percentage intensity difference between the intensity of the spectrum and the intensity of the bbc. The maximum deviation can be positive (such as a peak where the spectrum intensity is greater than the bbc) or negative (such as a trough where the spectrum intensity is less than the bbc). To make a meaningful comparison of the spectra, each spectra is normalized to have the same CIE 1931 XYZ relative luminance Y. The spectrum is normalized using the photopic luminosity function y(λ)—sometimes referred to as the photopic or visual luminous efficiency function v(λ)—of a standard observer which takes account of the photopic (visual) response of an observer and are for the same correlated color temperature. $I_{maxdev}$ is thus the maximum (greatest) percentage intensity difference between the normalized intensity of the spectrum and the normalized intensity of the bbc over a wavelength range from about 430 nm to 520 nm. $I_{maxdev}$ is defined as:

$$I_{maxdev} = \left[\frac{\text{Intensity of spectrum at } \lambda_{maxdev} \times 100}{\text{Intensity of } bbc \text{ at } \lambda_{maxdev}}\right] - 100$$

For example, referring to FIG. 5, for spectrum A the maximum deviation of the spectrum from the bbc corresponds to peak 580 at a wavelength $\lambda_{maxdev}$=455 nm. The intensity of the spectrum at $\lambda_{maxdev}$ is denoted 590 and the intensity of the bbc at $\lambda_{maxdev}$ is denoted 592. Therefore, using the calculation above, over the wavelength range from about 430 nm to about 520 nm, spectrum A has a maximum percentage intensity deviation $I_{maxdev}$ of 95%, that is at the maximum percentage intensity deviation the normalized intensity of spectrum A at wavelength $\lambda_{maxdev}$ is 195% of the normalized intensity of the bbc at the same wavelength. In contrast, spectrum B has a maximum percentage intensity deviation $I_{maxdev}$ of only 30% (corresponding to peak 582), that is the normalized intensity of spectrum A at wavelength $\lambda_{maxdev}$ is 130% of the normalized intensity of the bbc at this wavelength.

Roll-off wavelength, $\lambda_{RO}$, is defined as the wavelength at which the normalized intensity (I) decreases from its maximum intensity (denoted $I_{max}$) in the orange to region of the spectrum to half its maximum intensity (denoted ½ $I_{max}$). As described above, the maximum intensity $I_{max}$ within this wavelength region of the spectrum corresponds to photoluminescence converted light and the maximum intensity occurs at a wavelength longer than about 570 nm. For instance, the maximum intensity may occur at wavelength ranging from about 590 nm to about 620 nm.

Packaged White Light Emitting Device Test Method

The packaged test method involves measuring total light emission of a packaged white light emitting device (FIG. 3a) in an integrating sphere.

Packaged full spectrum white light emitting devices in accordance with the invention (Dev.#) each comprise a 2835 (2.8 mm×3.5 mm) SMD package containing three 1133 (11 mil by 33 mm) LED chips of dominant wavelength $\lambda_{d1}$=443 nm, $\lambda_{d2}$=451 nm and $\lambda_{d3}$=457 nm.

In this specification, the following nomenclature is used to denote white light emitting devices: Com.# denotes a comparative light emitting device in which each excitation source comprises one or more solid-state light sources of a single dominant wavelength and Dev.# denotes a white light emitting device in accordance with an embodiment of the invention in which each excitation source comprises solid-state light sources of two different dominant wavelengths.

2700K Full Spectrum White Light Emitting Devices Test Data

Tables 3, 4 and 5 tabulate measured optical test data for 2700K white light emitting devices Dev.1, Dev.2 and a known CRI90 comparative device Com.1 and illustrate the effect on efficacy of reducing the red spectral content while maintaining the blue and cyan spectral content.

Light emitting devices Dev.1 and Dev.2 each comprise a 2835 package containing three LED chips of dominant wavelength $\lambda_{d1}$=443 nm, $\lambda_{d2}$=451 nm and $\lambda_{d3}$=457 nm. Dev.1 comprises a combination of GAL520 and CASN650 phosphors and Dev.2 comprises a combination of GAL520, GAL530, CASN625 and CASN650 phosphors. The combination of CASN625 and CASN650 produces a peak emission of about 628 nm with the wavelength depending on the relative proportion of CASN625 to CASN650. Comparative device Com.1 comprises a known 2835 packaged white light emitting device which utilizes a narrow-band excitation source and has a nominal CRI Ra of 90.

Figure 6:
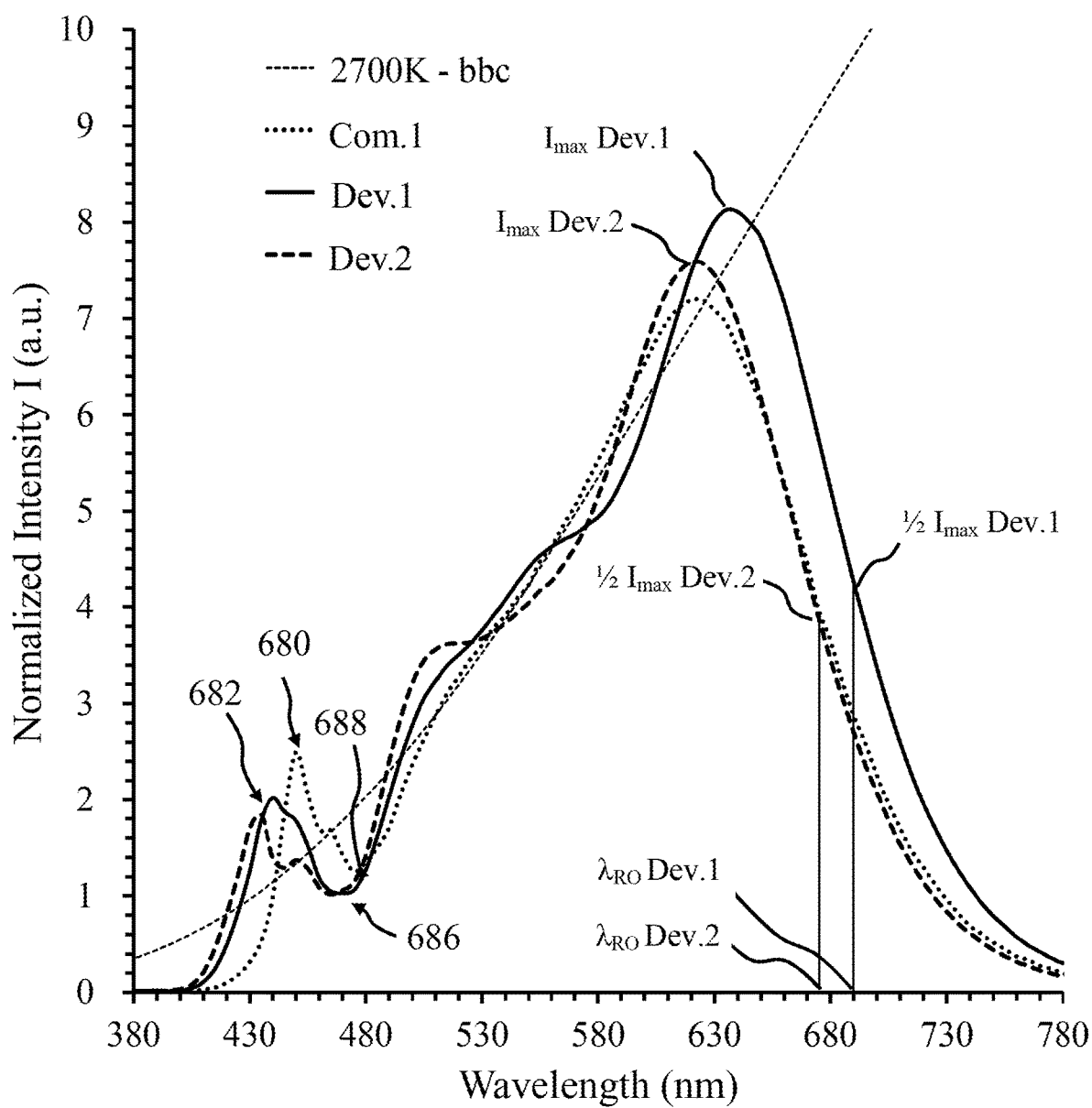
FIG. 6 are emission spectra, normalized intensity (normalized to a CIE 1931 XYZ relative luminance Y=100) versus wavelength (nm) for (i) Dev.1 (solid line), (ii) Dev.2 (thick dashed line), (iii) Com.1 (dotted line), and (iv) Plankian spectrum (thin dashed line) for a CCT of 2700K that is nominally the same as Dev.1, Dev.2, and Com.1.

FIG. 6 are emission spectra, normalized intensity (normalized to a CIE 1931 XYZ relative luminance Y=100) versus wavelength (nm) for (i) Dev. 1 (solid line), (ii) Dev. 2 (thick dashed line), (iii) Com.1 (dotted line), and (iv) Plankian spectrum (thin dashed line) for a CCT of 2700K that is nominally the same as Dev. 1, Dev. 2, and Com.1. To make a meaningful comparison of the spectra, each spectra has been normalized such each has a CIE 1931 XYZ relative luminance Y=100. The data are normalized using the CIE 1931 luminosity function y($\lambda$) of a standard observer which takes account of the photopic response of an observer. The Plankian spectrum (curve) or black-body curve in FIG. 6 represents the spectrum for a General CRI Ra equal to 100 for a given color temperature (CCT). Accordingly, for a white light emitting device of a given color temperature to have the highest color rendering possible, its emission spectrum should match as closely as possible the black-body spectrum of the same color temperature.

Referring to FIG. 6, it will be noted that the effect on the emission spectral energy content of devices Dev.1 and Dev.2 in accordance with the invention (comprising a broadband excitation source) compared with the comparative device Com.1 (comprising a narrow-band excitation source) are a significant reduction in the intensity of the blue emission peak 682 at about 430 nm and 440 nm respectively. As can be seen from the figure, the reduction of the blue emission peak 682 of devices Dev.1 and Dev.2 (compared with peak 680 of Com.1) results in the emission spectrum more closely resembling the Plankian spectrum (that is more closely resembling natural sunlight) over a wavelength range 430 nm to 520 nm (blue to cyan). More specifically, analysis of the spectra indicates that over a wavelength range 430 nm to 520 nm (blue to cyan), there is a maximum percentage normalized intensity deviation $I_{maxdev}$ of about 60% between the normalized intensity of light emitted by devices Dev.1 and Dev.2 and the normalized intensity of light of a black-body curve (bbc) of the same Correlated Color Temperature (2700K). That is Dev.1 and Dev.2 each generate light with an intensity that is 160% of the intensity of light of the bbc at the same wavelength. The maximum deviation in normalized intensity occurs at wavelengths $\lambda_{maxdev}$ at about 430 nm and about 440 nm respectively. This is to be contrasted with the known comparative device Com.1, that utilizes a narrowband excitation light source, which generates white light that exhibits a maximum percentage deviation $I_{maxdev}$ in normalized intensity of about 80% occurring at a wavelength $\lambda_{maxdev}$ of about 450 nm.

It will be appreciated that devices Dev.1 and Dev.2 thus produce white light that more closely resembles natural light over this wavelength region where human non-visual perception measured by CAF (Circadian Action Factor) are affected most and this can be beneficial to human wellbeing. It is believed that this change in spectral energy content resulting from the use of a broadband blue excitation source that at least partially fills the trough in the cyan region of the spectrum and reduces the peak overshoot in the blue region accounts for the superior color rendering properties of the devices of the invention. As can be seen from Table 3, devices Dev.1 and Dev.2 produce white light having a CAF that is within 1.9% and 0.8% respectively of that of natural light (bbc for a CCT 2700K). In comparison, comparative device Com.1 has a CAF that is within 3.8% of that of natural light.

Turning to the intensity roll-off (tail) of the spectra in the orange to red region of the spectrum (i.e. for wavelength longer than about 570 nm). For Dev.1, the maximum peak intensity ($I_{max}$ Dev.1) is about 8.2 and this occurs at a wavelength of about 640 nm. The intensity (I) drops to half this value (½ $I_{max}$ Dev.1) at a wavelength ($\lambda_{RO}$ Dev. 1) of about 690 nm.

For Dev.2 the maximum peak intensity ($I_{max}$ Dev.2) is about 7.6 and this occurs at a wavelength of about 620 nm. The intensity (I) drops to half this value (½ $I_{max}$ Dev.2) at a wavelength ($\lambda_{RO}$ Dev. 2) of about 675 nm.

TABLE 3

2700K white light emitting devices—Measured test data (bbc = black-body curve)

| | | | Maximum deviation | | | |
|---|---|---|---|---|---|---|
| Device | Efficacy (lm/W) | Efficacy (%) | $I_{maxdev}$ (%) | $\lambda_{maxdev}$ (nm) | $\lambda_{RO}$ (nm) | CAF | CAF (%) |
| Com. 1 | 123 | — | 80 | 450 | 675 | 0.354 | 96.2 |
| Dev. 1 | 104 | 100 | 60 | 440 | 690 | 0.361 | 98.1 |
| Dev. 2 | 119 | 115 | 60 | 435 | 675 | 0.371 | 100.8 |
| bbc | N/A | N/A | N/A | N/A | N/A | 0.368 | 100.0 |

TABLE 4

2700K white light emitting devices—Measured test data

| | CIE Color Rendering CRI | | | | | | | | |
|---|---|---|---|---|---|---|---|---|---|
| Device | R1 | R2 | R3 | R4 | R5 | R6 | R7 | R8 | R9 |
| Com. 1 | 90.7 | 98.3 | 95.5 | 93.1 | 90.1 | 92.4 | 93.7 | 80.7 | 53.7 |
| Dev. 1 | 97.7 | 99.0 | 93.7 | 93.7 | 97.3 | 99.4 | 96.8 | 97.2 | 98.2 |
| Dev. 2 | 99.1 | 99.3 | 98.1 | 96.5 | 98.1 | 94.9 | 93.9 | 86.6 | 69.6 |

TABLE 5

2700K white light emitting devices—Measured test data

| | CIE Color Rendering CRI | | | | | | |
|---|---|---|---|---|---|---|---|
| Device | R10 | R11 | R12 | R13 | R14 | R15 | Ra |
| Com. 1 | 84.2 | 94.0 | 79.7 | 91.0 | 96.7 | 85.9 | 91.2 |
| Dev. 1 | 96.6 | 91.2 | 95.2 | 98.5 | 95.5 | 98.4 | 96.9 |
| Dev. 2 | 98.1 | 91.0 | 89.5 | 99.3 | 98.9 | 93.1 | 95.8 |

Referring to Tables 3, 4 and 5 it is to be noted that device Dev.1 has an efficacy of 104 lm/W and produces white light with a CRI Ra greater than or equal to 95 (96.9) with each of CRI R1 to CRI R15 being 90 or higher (91.2 to 99.0). In comparison, device Dev.2 has an efficacy of 119 lm/W and produces white light with a CRI Ra greater than or equal to 95 (95.8) in which CRI R1 to CRI R7 and CRI R10 to CRI R15 are about 90 or higher (89.5 to 99.3), while CRI R8 (corresponding to "Reddish Purple") is greater than 72 and less than 90 (86.6), while CRI R9 (corresponding to "Saturated Red") is greater than 50 and less than 90 (69.6). Further, it is to be noted that while the quality of light produced by Dev.2 is substantially the same as that of Dev.1, the efficacy increases substantially by about 15% (from 104 lm/W to 119 lm/W).

It will be appreciated from FIG. 6 and Table 3 that the increase in efficacy of Dev.2 compared with Dev.1 is a direct result of the spectral roll-off of Dev.2 occurring at a shorter wavelength (675 nm) than that of Dev.1 (690 nm).

3000K Full Spectrum White Light Emitting Devices Test Data

Tables 6, 7 and 8 tabulate measured optical test data for 3000K white light emitting devices Dev.3 to Dev.5 and known 3000K CRI90 and CRI80 comparative devices Com.2 and Com.3 respectively and illustrate the effect on efficacy of reducing the red spectral content while maintaining the blue and cyan spectral content.

Light emitting devices Dev.3 to Dev.5 each comprise a 2835 package containing three LED chips of dominant wavelength $\lambda_{d1}$=443 nm, $\lambda_{d2}$=451 nm and $\lambda_{d1}$=457 nm. Dev.3 comprises a combination of GAL520 and CASN650 phosphors while devices Dev.4 and Dev.5 a combination of GAL520, GAL530, CASN625 and CASN650 phosphors in which Dev.5 comprises a greater relative portion of CASN625 to CASN650 than Dev.4 (the combination of CASN625 and CASN650 in Dev.4 produces a peak emission of about 625 nm and the combination in Dev.5 produces a peak emission of about 628 nm). Comparative device Com.2 comprises a known 2835 packaged white light emitting device which utilizes a narrow-band excitation source and has a nominal CRI Ra of 90. Com.3 comprises a known 2835 packaged white light emitting device which utilizes a narrowband excitation source and has a nominal CRI Ra of 80.

Figure 7A:
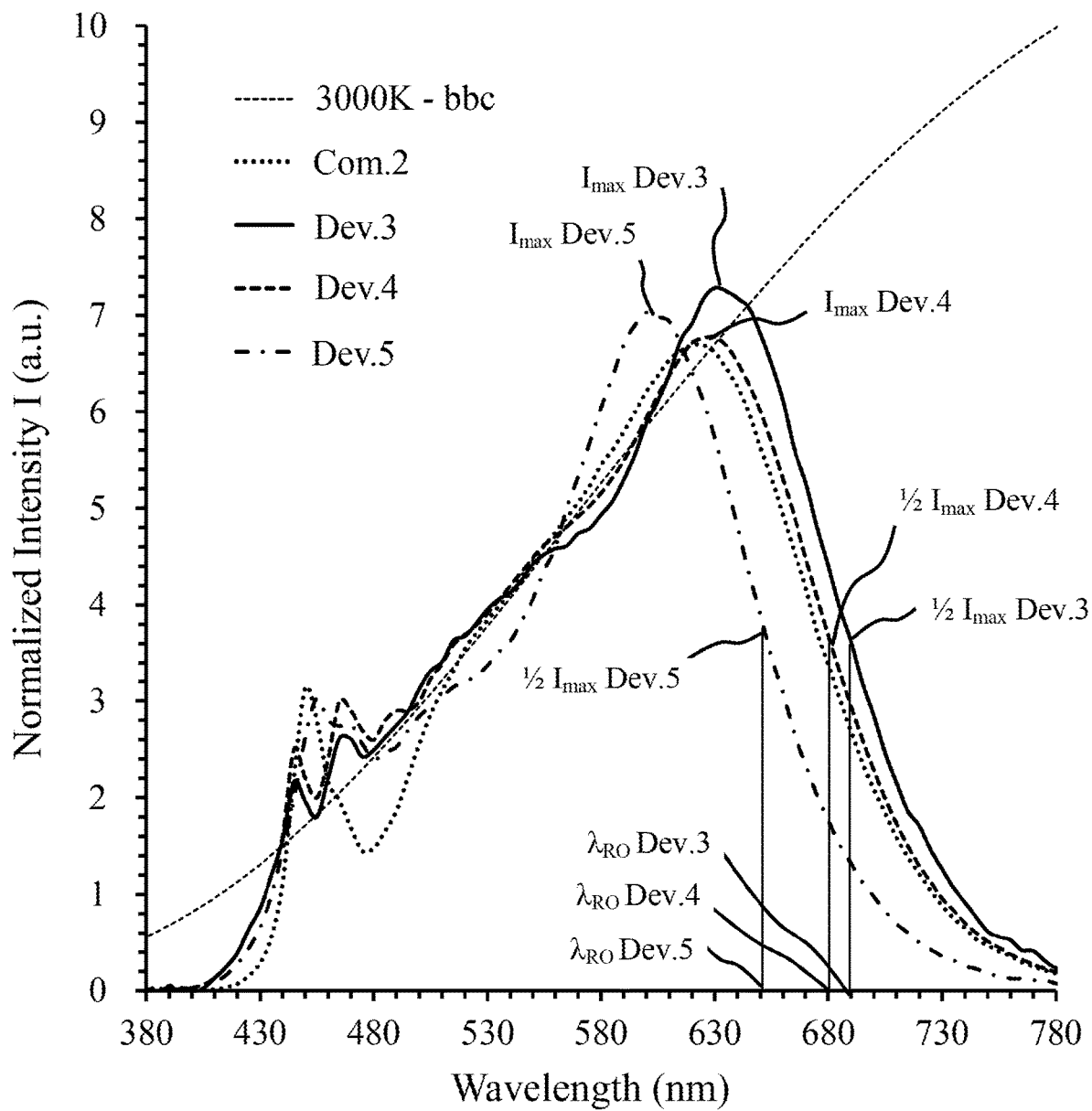
FIG. 7a are emission spectra, normalized intensity (normalized to a CIE 1931 XYZ relative luminance Y=100) versus wavelength (nm) for (i) Dev.3 (solid line), (ii) Dev.4 (thick dashed line), (iii) Dev.5 (dash dot line), (iv) Com.2 (dotted line), and (v) Plankian spectrum (thin dashed line) for a CCT of 3000K that is nominally the same as Dev.3, Dev.4, Dev.5 and Com.2.
Figure 7B:
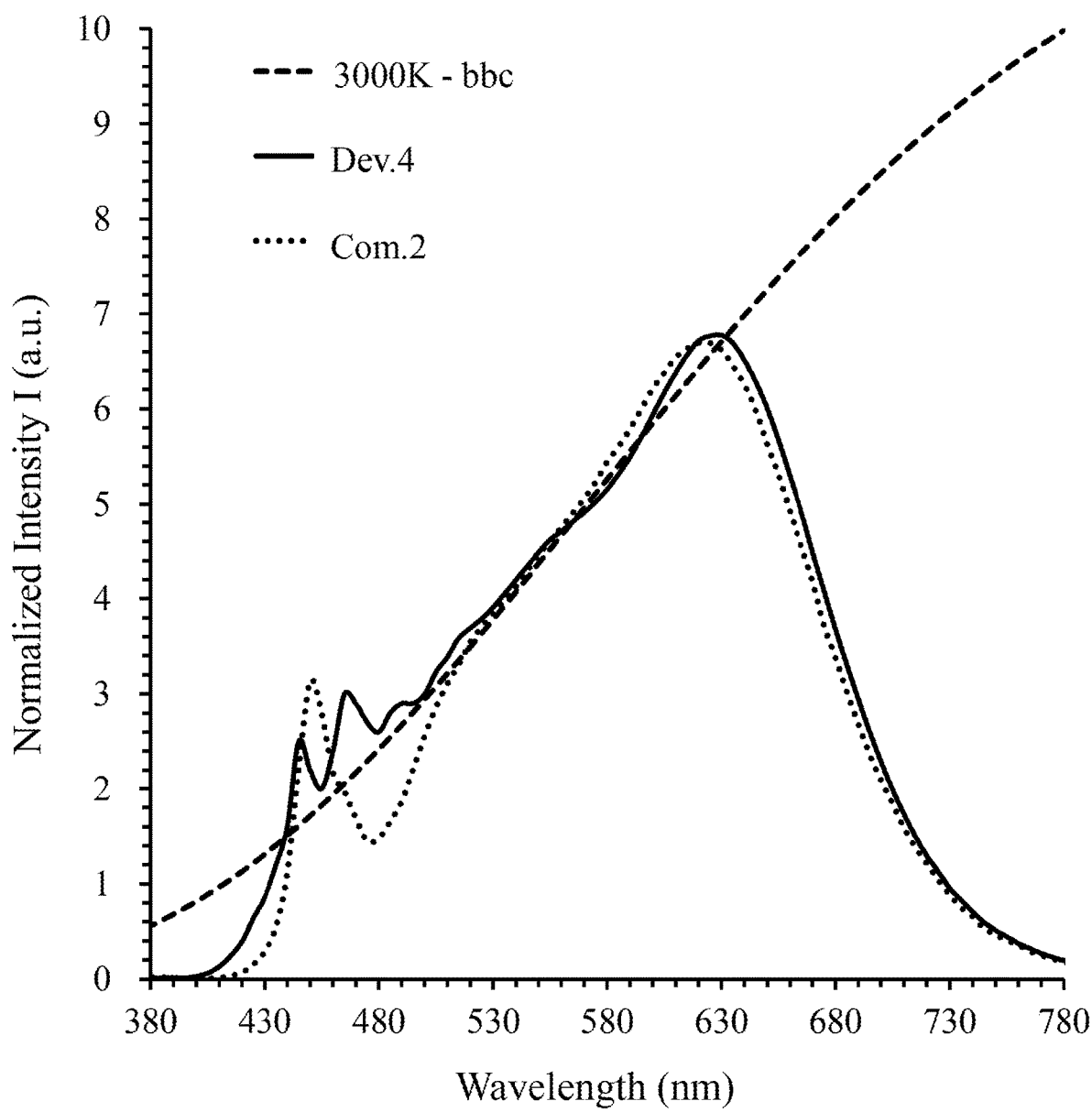
FIG. 7b are emission spectra, normalized intensity (normalized to a CIE 1931 XYZ relative luminance Y=100) versus wavelength (nm) for (i) Dev.4 (solid line), (ii) Com.2 (dotted line), and (iii) Plankian spectrum (dashed line) for a CCT of 3000K that is nominally the same as Dev.4 and Com.2.
Figure 7C:
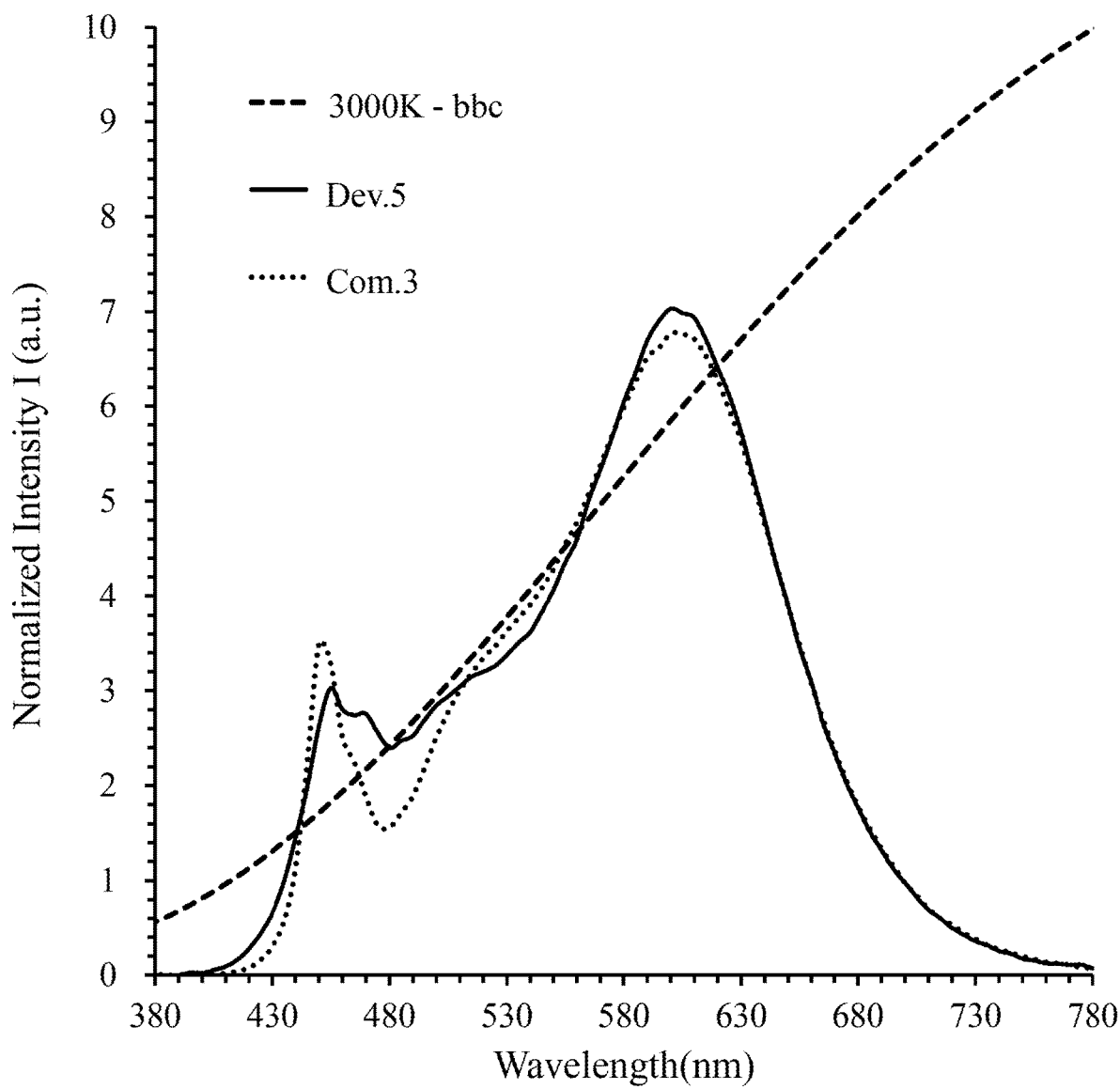
FIG. 7c are emission spectra, normalized intensity (normalized to a CIE 1931 XYZ relative luminance Y=100) versus wavelength (nm) for (i) Dev.5 (solid line), (ii) Com.3 (dotted line), and (iii) Plankian spectrum (dashed line) for a CCT of 3000K that is nominally the same as Dev.5 and Com.3.

FIG. 7a are emission spectra, normalized intensity (normalized to a CIE 1931 XYZ relative luminance Y=100) versus wavelength (nm) for (i) Dev. 3 (solid line), (ii) Dev. 4 (thick dashed line), (iii) Dev.5 (dash dot line), (iv) Com.2 (dotted line), and (v) Plankian spectrum or black-body curve (thin dashed line) for a CCT of 3000K that is nominally the same as Dev.3, Dev.4, Dev.5 and Com.2. FIG. 7b are emission spectra, normalized intensity (normalized to a CIE 1931 XYZ relative luminance Y=100) versus wavelength (nm) for (i) Dev.4 (solid line), (ii) Com.2 (dotted line), and (iii) Plankian spectrum (dashed line) for a CCT of 3000K that is nominally the same as Dev.4 and Com.2. FIG. 7c are emission spectra, normalized intensity (normalized to a CIE 1931 XYZ relative luminance Y=100) versus wavelength (nm) for (i) Dev.5 (solid line), (ii) Com.3 (dotted line), and (iii) Plankian spectrum (dashed line) for a CCT of 3000K that is nominally the same as Dev.5 and Com.3. Analysis of the spectrum indicates that over a wavelength range 430 nm to 520 nm (blue to cyan), a maximum percentage normalized intensity deviation $I_{maxdev}$ of about 40%, about 50% and about 60% between the normalized intensity of light emitted by devices Dev.3, Dev.4 and Dev.5 normalized intensity of light of a black-body curve of the same Correlated Color Temperature (3000K). This is to be contrasted with the known comparative devices Com.2 and Com.3, that utilizes a narrowband excitation light source, which generate white light that exhibits a maximum percentage deviation $I_{maxdev}$ in normalized intensity of about 70% and 100% respectively (at a wavelength of about 450 nm). Moreover, as can be seen from Table 6 devices Dev.3, Dev.4 and Dev.5 produce white light having a CAF that is within 3.4%, 4.1% and 3.4% of that of natural light (bbc for a CCT 3000K). In comparison, comparative devices Com.2 and Com.3 have a CAF that is only within 11.5% and 9.5% respectively of that of natural light.

It will be appreciated that each of devices Dev.3, Dev.4 and Dev.5 thus produce white light that more closely resembles natural light over this wavelength region where human non-visual perception measured by CAF (Circadian Action Factor) or Melanopic Ratio (MR) are affected most and this can be beneficial to human wellbeing.

Turning to the intensity roll-off (tail) of the spectra in the orange to red region of the spectrum (i.e. for wavelength longer than about 570 nm). For Dev.3 the maximum peak intensity ($I_{max}$ Dev.3) is about 7.3 and this occurs at a wavelength of about 630 nm. The intensity (I) drops to half this value (½ $I_{max}$ Dev.3) at a wavelength ($\lambda_{RO}$ Dev.3) of about 690 nm.

For Dev.4 the maximum peak intensity ($I_{max}$ Dev.4) is about 6.8 and this occurs at a wavelength of about 625 nm. The intensity (I) drops to half this value (½ $I_{max}$ Dev.4) at a wavelength ($\lambda_{RO}$ Dev.4) of about 680 nm.

For Dev.5 the maximum peak intensity ($I_{max}$ Dev.5) is about 7.0 and this occurs at a wavelength of about 605 nm. The intensity (I) drops to half this value (½ $I_{max}$ Dev.5) at a wavelength ($\lambda_{RO}$ Dev.5) of about 650 nm.

TABLE 6

3000K white light emitting devices—Measured test data (bbc = black-body curve)

| Device | Efficacy (lm/W) | Efficacy (%) | Maximum deviation $I_{maxdev}$ (%) | $\lambda_{maxdev}$ (nm) | $\lambda_{RO}$ (nm) | CAF | CAF (%) |
|---|---|---|---|---|---|---|---|
| Com. 2 | 127 | — | 70 | 450 | 680 | 0.386 | 88.5 |
| Dev. 3 | 109 | 100 | 40 | 445 | 690 | 0.451 | 103.4 |
| Dev. 4 | 120 | 110 | 50 | 445 | 680 | 0.454 | 104.1 |
| Com. 3 | 144 | — | 100 | 450 | 655 | 0.395 | 90.5 |
| Dev. 5 | 149 | 137 | 60 | 455 | 650 | 0.451 | 103.4 |
| bbc | N/A | N/A | N/A | N/A | N/A | 0.436 | 100.0 |

TABLE 7

3000K white light emitting devices—Measured test data

| | CIE Color Rendering CRI | | | | | | | | |
|---|---|---|---|---|---|---|---|---|---|
| Device | R1 | R2 | R3 | R4 | R5 | R6 | R7 | R8 | R9 |
| Com. 2 | 91.2 | 94.5 | 97.4 | 92.0 | 90.6 | 93.7 | 92.9 | 81.1 | 55.9 |
| Dev. 3 | 98.2 | 97.9 | 92.2 | 93.1 | 97.4 | 97.6 | 95.1 | 95.3 | 96.2 |
| Dev. 4 | 97.1 | 97.0 | 95.7 | 95.8 | 96.7 | 96.6 | 95.2 | 90.8 | 77.8 |
| Com. 3 | 81.1 | 90.7 | 96.5 | 79.9 | 80.7 | 87.9 | 83.7 | 61.2 | 12.4 |
| Dev. 5 | 84.2 | 94.5 | 93.0 | 83.6 | 85.5 | 95.1 | 82.2 | 60.0 | 11.9 |

TABLE 8

3000K white light emitting devices—Measured test data

| | CIE Color Rendering CRI | | | | | | |
|---|---|---|---|---|---|---|---|
| Device | R10 | R11 | R12 | R13 | R14 | R15 | Ra |
| Com. 2 | 86.8 | 92.6 | 76.8 | 91.9 | 97.9 | 86.5 | 91.7 |
| Dev. 3 | 94.2 | 91.8 | 93.3 | 99.3 | 94.9 | 98.0 | 95.9 |
| Dev. 4 | 92.4 | 95.9 | 91.6 | 97.0 | 96.9 | 94.6 | 95.6 |
| Com. 3 | 78.4 | 78.5 | 66.3 | 83.3 | 98.6 | 74.5 | 82.7 |
| Dev. 5 | 88.7 | 84.9 | 85.6 | 87.0 | 96.5 | 75.4 | 85.0 |

Referring to Tables 6, 7 and 8, it is to be noted that device Dev.3 has an efficacy of 109 lm/W and produces white light with a CRI Ra greater than 95 (95.9) with each of CRI R1 to CRI R15 is 90 or higher (91.8 to 99.3). In comparison, device Dev.4 has a efficacy of 149 lm/W and produces white light with a CRI Ra greater than 95 (95.6) with each of CRI R1 to CRI R8 and CRI R10 to CRI R15 is 90 or higher while CRI R9 (corresponding to "Saturated Red") is greater than 50 and less than 90 (77.8). In comparison, device Dev.5 has a efficacy of 120 lm/W and produces white light with a CRI Ra greater than or equal to 85 (85.0) with each of CRI R1 to CRI R7 and CRI R10 to CRI R15 is 90 or higher, while CRI R8 (corresponding to "Reddish Purple") is less than 72 (60.0), while CRI R9 (corresponding to "Saturated Red") is greater than 10 and less than 90 (11.9). Further, it is to be noted that while the quality of light produced by Dev.4 and Dev.5 are substantially the same as that of Dev.3 the efficacy increases substantially by about 20% and 50% respectively.

4000K Full Spectrum White Light Emitting Devices Test Data

Tables 9, 10 and 11 tabulate measured optical test data for 4000K white light emitting devices Dev.6 and a known 4000K CRI90 comparative device Com.4. Light emitting device Dev.6 comprises a 2835 package containing three LED chips of dominant wavelength $\lambda_{d1}$=443 nm, $\lambda_{d2}$=451 nm and $\lambda_{d1}$=457 nm and comprises a combination of GAL520 and CASN650 phosphors. Comparative device Com.4 comprises a known 2835 packaged white light emitting device which utilizes a narrowband excitation source and has a nominal CRI Ra of 90.

Figure 8:
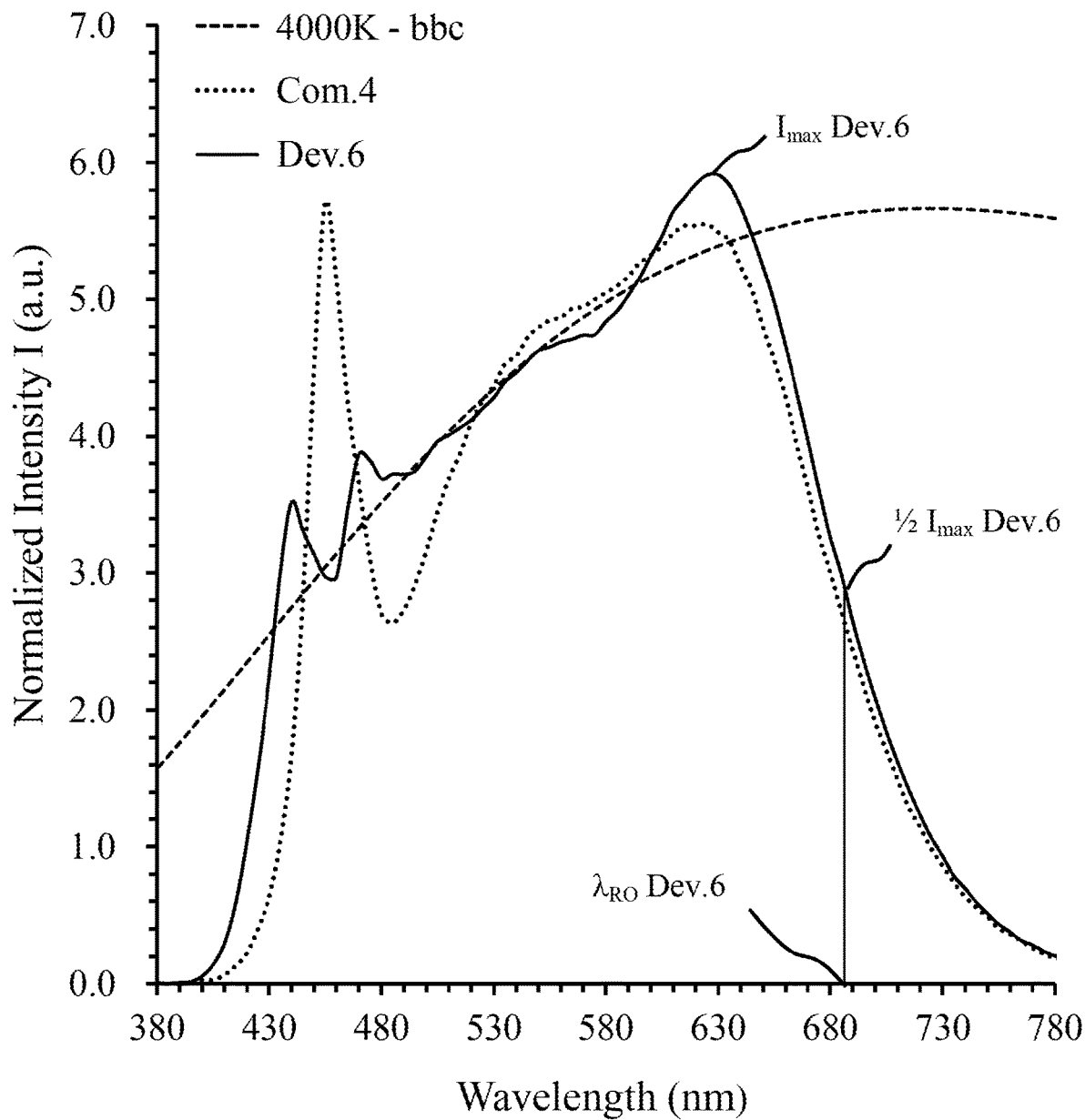
FIG. 8 are emission spectra, normalized intensity (normalized to a CIE 1931 XYZ relative luminance Y=100) versus wavelength (nm) for (i) Dev.6 (solid line), (ii) Com.4 (dotted line), and (iii) Plankian spectrum (dashed line) for a CCT of 4000K that is nominally the same as Dev.6 and Com.4.

FIG. 8 are emission spectra, normalized intensity (normalized to a CIE 1931 XYZ relative luminance Y=100) versus wavelength (nm) for (i) Dev.6 (solid line), (ii) Com.4 (dotted line), and (v) Plankian spectrum (dashed line) for a CCT of 4000K that is nominally the same as Dev. 6 and Com.3. Analysis of the spectrum indicates that over a wavelength range 430 nm to 520 nm (blue to cyan), a maximum percentage normalized intensity deviation $I_{maxdev}$ of about 30%, that is the maximum difference between the normalized intensity of light emitted by devices Dev.6 normalized intensity of light of a black-body curve (bbc) of the same Correlated Color Temperature (4000K). This is to be contrasted with the known comparative device Com.2, that utilizes a narrowband excitation light source, which generate white light that exhibits a maximum percentage deviation $I_{maxdev}$ in normalized intensity of about 90% (at a wavelength of about 450 nm). Moreover, As can be seen from Table 6 devices Dev.6 generates white light having a CAF that is 0.4% of that of natural light (bbc for a CCT 4000K). In comparison comparative device Com.3 has a CAF that is only within 7.0% of that of natural light.

It will be appreciated that device Dev.6 produces white light that more closely resembles natural light over this wavelength region where human non-visual perception measured by CAF (Circadian Action Factor) or Melanopic Ratio (MR) are affected most and this can be beneficial to human wellbeing.

Turning to the intensity roll-off (tail) of the spectra in the orange to red region of the spectrum (i.e. for wavelength longer than about 570 nm). For Dev.6 the maximum peak intensity ($I_{max}$ Dev.6) is about 5.9 and this occurs at a wavelength of about 630 nm. The intensity (I) drops to half this value (½ $I_{max}$ Dev.6) at a wavelength ($\lambda_{RO}$ Dev.6) of about 685 nm.

TABLE 9

4000K white light emitting device—Measured test data
(bbc = black-body curve)

| Device | Efficacy (lm/W) | Maximum deviation | | | | CAF (%) |
|---|---|---|---|---|---|---|
| | | $I_{maxdev}$ (%) | $\lambda_{maxdev}$ (nm) | $\lambda_{RO}$ (nm) | CAF | |
| Com. 4 | 133 | 90 | 450 | 680 | 0.599 | 93.0 |
| Dev. 6 | 117 | 30 | 440 | 685 | 0.646 | 99.6 |
| bbc | N/A | N/A | N/A | N/A | 0.644 | 100.0 |

TABLE 10

4000K white light emitting device—Measured test data

CIE Color Rendering CR1

| Device | R1 | R2 | R3 | R4 | R5 | R6 | R7 | R8 | R9 |
|---|---|---|---|---|---|---|---|---|---|
| Com. 4 | 95.0 | 96.9 | 96.8 | 92.5 | 92.7 | 93.9 | 95.4 | 91.1 | 79.2 |
| Dev. 6 | 98.5 | 98.8 | 96.2 | 97.7 | 98.7 | 98.5 | 97.9 | 96.5 | 93.3 |

TABLE 11

4000K white light emitting device—Measured test data

CIE Color Rendering CRI

| Device | R10 | R11 | R12 | R13 | R14 | R15 | Ra |
|---|---|---|---|---|---|---|---|
| Com. 4 | 90.9 | 93.0 | 67.7 | 95.6 | 97.7 | 92.5 | 94.3 |
| Dev. 6 | 97.3 | 97.3 | 94.9 | 98.4 | 97.3 | 97.7 | 97.8 |

Referring to Tables 9, 10 and 11, it is to be noted that device Dev.6 has an efficacy of 117 lm/W and produces white light with a CRI Ra greater than 95 (95.9) with each of CRI R1 to CRI R15 is 90 or higher (91.8 to 99.3).

5000K Full Spectrum White Light Emitting Devices Test Data

Tables 12, 13 and 14 tabulate measured optical test data for 5000K white light emitting devices Dev.7 and Dev.8 and known 5000K CRI90 and CRI80 comparative devices Com.5 and Com.6 respectively and illustrate the effect on efficacy of reducing the red spectral content while maintaining the blue and cyan spectral content.

Light emitting devices Dev.7 and Dev.8 each comprise a 2835 package containing three LED chips of dominant wavelength $\lambda_{d1}$=443 nm, $\lambda_{d2}$=451 nm and $\lambda_{d1}$=457 nm. Dev.7 comprises a combination of GAL520 and CASN650 phosphors while devices Dev.8 a combination of GAL520, GAL530, CASN625 and CASN650 phosphors. Comparative device Com.5 comprises a known 2835 packaged white light emitting device which utilizes a narrowband excitation source and has a nominal CRI Ra of 90. Com.6 comprises a known 2835 packaged white light emitting device which utilizes a narrowband excitation source and has a nominal CRI Ra of 80.

Figure 9A:
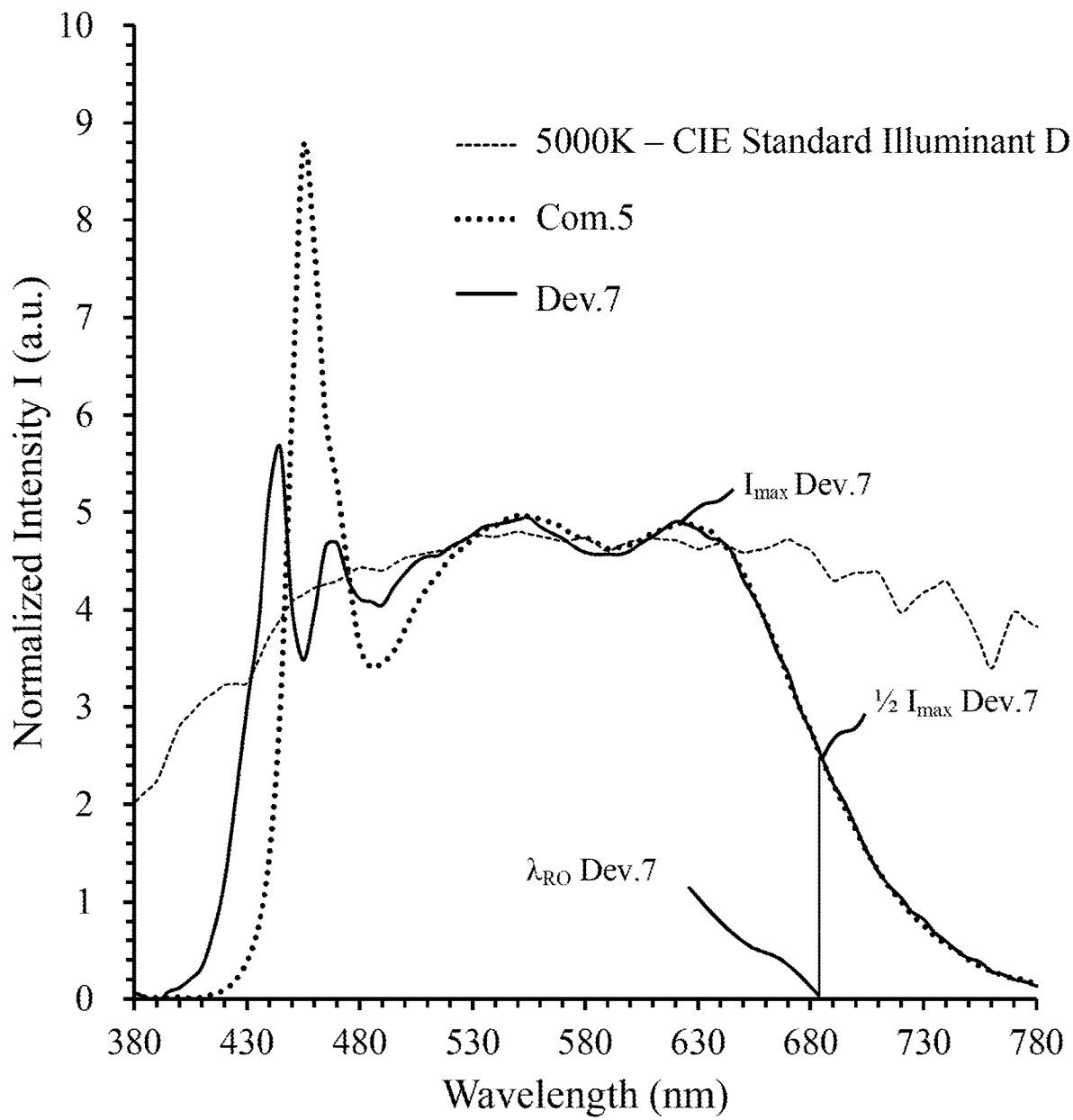
FIG. 9a are emission spectra, normalized intensity (normalized to a CIE 1931 XYZ relative luminance Y=100) versus wavelength (nm) for (i) Dev.7 (solid line), (ii) Com.5

FIG. 9a are emission spectra, normalized intensity (normalized to a CIE 1931 XYZ relative luminance Y=100) versus wavelength (nm) for (i) Dev.7 (solid line), (ii) Com.5 (dotted line), and (iii) Plankian spectrum (dashed line) for a CCT of 5000K that is nominally the same as Dev.7 and Com.5. Analysis of the spectrum indicates that over a wavelength range 430 nm to 520 nm (blue to cyan), a maximum percentage normalized intensity deviation $I_{maxdev}$ of about 50% between the normalized intensity of light emitted by devices Dev.7 normalized intensity of light of the CIE Standard Illuminant D of the same Correlated Color Temperature (5000K). This is to be contrasted with the known comparative device Com.5, that utilizes a narrowband excitation light source, which generate white light that exhibits a maximum percentage deviation $I_{maxdev}$ in normalized intensity of about 115% (at a wavelength $\lambda_{maxdev}$ of about 450 nm). Moreover, As can be seen from Table 12 device Dev.7 produces white light having a CAF that is within 2.1% of that of natural light (CIE D for a CCT 5000K). In comparison comparative device Com.5 has a CAF that is only within 12.6% of that of natural light.

Figure 9B:
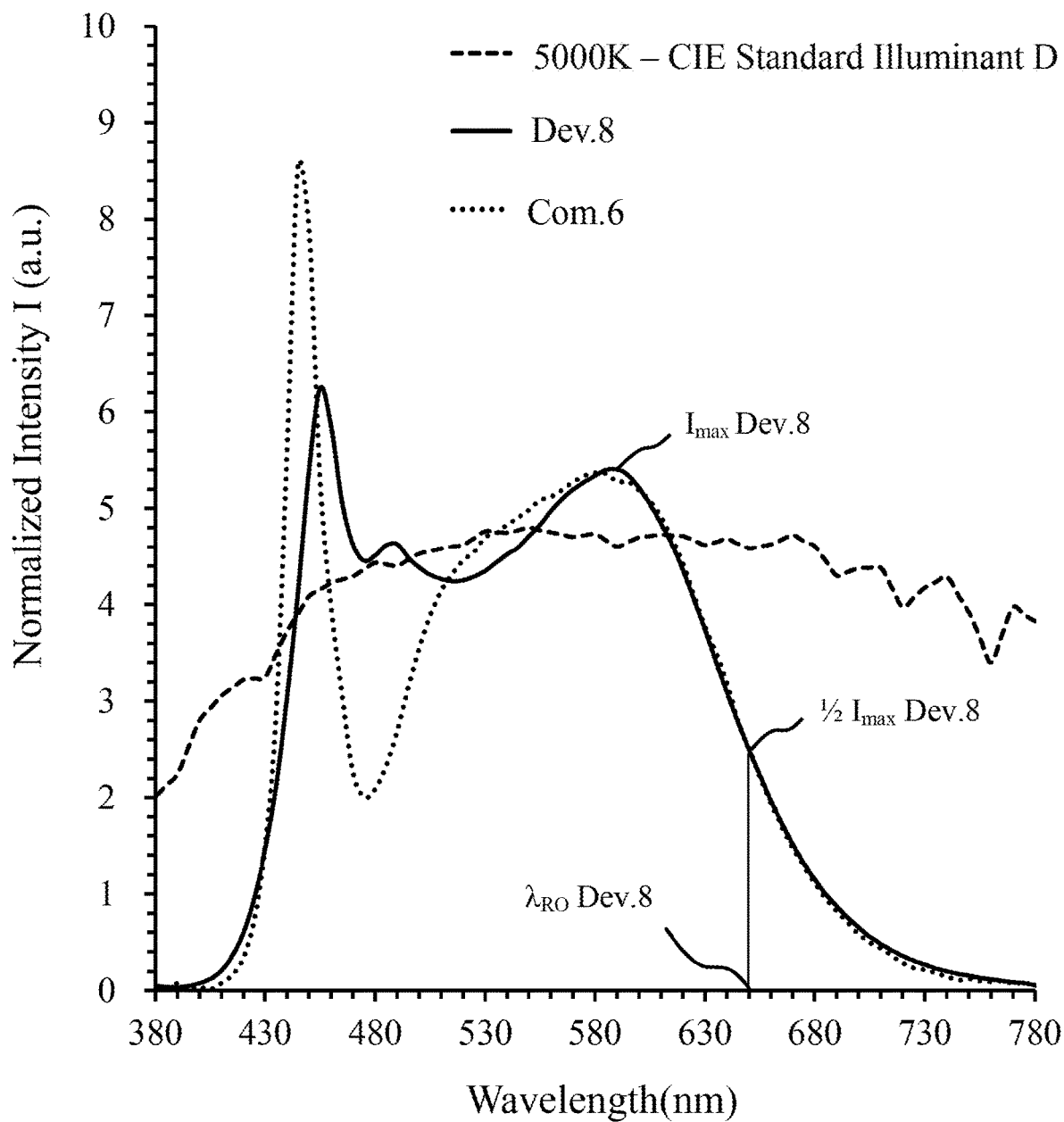
FIG. 9b are emission spectra, normalized intensity (normalized to a CIE 1931 XYZ relative luminance Y=100) versus wavelength (nm) for (i) Dev.8 (solid line), (ii) Com.6 (dotted line), and (iii) Plankian spectrum (dashed line) for a CCT of 5000K that is nominally the same as Dev.8 and Com.6.

FIG. 9b are emission spectra, normalized intensity (normalized to a CIE 1931 XYZ relative luminance Y=100) versus wavelength (nm) for (i) Dev.8 (solid line), (ii) Com.6 (dotted line), and (iii) Plankian spectrum (dashed line) for a CCT of 5000K that is nominally the same as Dev.8 and Com.6. Analysis of the spectrum indicates that over a wavelength range 430 nm to 520 nm (blue to cyan), a maximum percentage normalized intensity deviation $I_{maxdev}$ of about 20% between the normalized intensity of light emitted by devices Dev.8 and the normalized intensity of light of the CIE Standard Illuminant D of the same Correlated Color Temperature (5000K). This is to be contrasted with the known comparative device Com.6, that utilizes a narrowband excitation light source, which generate white light that exhibits a maximum percentage normalized intensity deviation of about 140% (at a wavelength $\lambda_{maxdev}$ of about 450 nm). Moreover, As can be seen from Table 12 device Dev.8 produces white light having a CAF that is within 2.0% of that of natural light (CIE D for a CCT 5000K). In comparison comparative device Com.6 has a CAF that is only within 13.1% of that of natural light.

It will be appreciated that each of devices Dev.7 and Dev.8 produce white light that more closely resembles natural light over this wavelength region where human non-visual perception measured by CAF (Circadian Action Factor) or Melanopic Ratio (MR) are affected most and this can be beneficial to human wellbeing.

Turning to the intensity roll-off (tail) of the spectra in the orange to red region of the spectrum (i.e. for wavelength longer than about 570 nm). For Dev.7 the maximum peak intensity ($I_{max}$ Dev.7) is about 4.9 and this occurs at a wavelength of about 625 nm. The intensity (I) drops to half this value (½ $I_{max}$ Dev.7) at a wavelength ($\lambda_{RO}$ Dev.7) of about 685 nm.

For Dev.8 the maximum peak intensity ($I_{max}$ Dev.8) is about 5.6 and this occurs at a wavelength of about 590 nm. The intensity (I) drops to half this value (½ $I_{max}$ Dev.8) at a wavelength ($\lambda_{RO}$ Dev.8) of about 650 nm.

TABLE 12

5000K white light emitting devices—Measured test data (bbc = black-body curve)

| Device | Efficacy (lm/W) | Efficacy (%) | Maximum deviation $I_{maxdev}$ (%) | $\lambda_{maxdev}$ (nm) | $\lambda_{RO}$ (nm) | CAF | CAF (%) |
|---|---|---|---|---|---|---|---|
| Com. 5 | 135 | — | 115 | 460 | 685 | 0.753 | 87.4 |
| Dev. 7 | 117 | 100 | 50 | 445 | 685 | 0.824 | 102.1 |
| Com. 6 | 165 | — | 140 | 445 | 645 | 0.701 | 86.9 |
| Dev. 8 | 152 | 130 | 20 | 455 | 650 | 0.791 | 98.0 |
| bbc | N/A | N/A | N/A | N/A | N/A | 0.807 | 100.0 |

TABLE 13

5000K white light emitting devices—Measured test data

CIE Color Rendering CRI

| Device | R1 | R2 | R3 | R4 | R5 | R6 | R7 | R8 | R9 |
|---|---|---|---|---|---|---|---|---|---|
| Com. 5 | 96.0 | 99.1 | 98.3 | 88.8 | 92.4 | 95.7 | 91.4 | 90.5 | 87.1 |
| Dev. 7 | 98.3 | 98.8 | 98.8 | 98.5 | 98.7 | 98.9 | 98.7 | 97.6 | 93.5 |
| Com. 6 | 82.4 | 87.6 | 90.8 | 83.9 | 82.2 | 81.8 | 89.9 | 73.5 | 23.5 |
| Dev. 8 | 82.4 | 93.5 | 93.4 | 81.1 | 83.9 | 90.6 | 83.9 | 62.6 | 1.3 |

TABLE 14

5000K white light emitting devices—Measured test data

CIE Color Rendering CRI

| Device | R10 | R11 | R12 | R13 | R14 | R15 | Ra |
|---|---|---|---|---|---|---|---|
| Com. 5 | 97.3 | 90.7 | 64.6 | 97.5 | 99.4 | 92.1 | 94.0 |
| Dev. 7 | 98.6 | 99.0 | 96.4 | 98.0 | 98.8 | 97.3 | 98.5 |
| Com. 6 | 70.0 | 82.4 | 56.0 | 83.5 | 95.0 | 78.2 | 84.0 |
| Dev. 8 | 85.2 | 81.2 | 73.1 | 85.9 | 96.4 | 75.0 | 83.9 |

Referring to Tables 12, 13 and 14 it is to be noted that device Dev.7 has an efficacy of 117 lm/W and produces white light with a CRI Ra greater than 95 (98.5) in which each of CRI R1 to CRI R15 is 90 or higher (93.5 to 99.0). In comparison, device Dev.8 has an efficacy of 152 lm/W and produces white light with a CRI Ra greater than 80 (83.9), while CRI R8 (corresponding to "Reddish Purple") is less than 72 (62.6), while CRI R9 (corresponding to "Saturated Red") is greater than zero and less than 90 (1.3). Further, it is to be noted that while the quality of light produced by Dev.8 is substantially the same as that of Dev.7 the efficacy increase substantially by about 30% and is comparable with Com.6.

As described above, a particular advantage of the present invention is that full spectrum white light emitting devices according to embodiments of the invention can generate full spectrum light that closely resembles natural light in blue to cyan (430 nm to 520 nm) region where human non-visual perception measured by CAF (Circadian Action Factor) or Melanopic Ratio (MR) are affected most. There has been much discussion in the lighting industry regarding blue light stimulation and its impact on circadian rhythm. The amount of blue to cyan light in a light source impacts melatonin secretion which can impact the circadian cycle. High levels of blue to cyan light suppress melatonin secretion, energizing the human body. Low levels of blue light do not suppress melatonin secretion, relaxing the human body. One metric used to estimate this non-visual effect is the CAF Circadian Action Factor, which typically is modulated by blue content throughout the day. At noon time the sun has a high CCT and higher blue to cyan content. Sunrise and sunset have a lower CCT and lower blue to cyan content. CAF value of natural light at a different CCT is a good measure of the lighting deviation from the nature light in blue to cyan region where human emotional, health, or wellbeing life are affected.

In summary, it will be appreciated that light emitting devices in accordance with the invention comprising a broadband solid-state excitation source enable the implementation of full spectrum white light emitting devices that are characterized by generating white light having a color temperature in a range 1800K to 6800K with one or more of (i) over a wavelength range from about 430 nm to about 520 nm, the maximum percentage intensity deviation of light emitted by the device is less than 60% from the intensity of light of a black-body curve or CIE Standard Illuminant D of the same Correlated Color Temperature, (ii) a spectrum having a CAF that is within 5%, 4%, 2%, or 1% of the black-body curve/CIE Standard Illuminant D; (iii) a CRI R9 and/or a CRI R8 that less than 90, (iv) a spectrum whose intensity decreases from its maximum value in the orange to red region of the spectrum to about 50% of said maximum value at a wavelength in a range from about 645 nm to about 695 nm, (v) a spectrum whose intensity decreases from its maximum value in the orange to red region of the spectrum to about 50% of said maximum value at a wavelength in a range from about 645 nm to about 695 nm and has a CRI Ra greater than or equal to 85, CRI R1 to CRI R7 and CRI R10 to CRI R15 greater than or equal to 90, CRI R8 less than 72, and CRI R9 greater than 10 and less than 90, (vi) a spectrum whose intensity decreases from its maximum value in the orange to red region of the spectrum to about 50% of said maximum value at a wavelength in a range from about 645 nm to about 695 nm and has a CRI Ra greater than or equal to 95, CRI R1 to CRI R8 and CRI R10 to CRI R15 greater than or equal to 90, and CRI R9 greater than 50 and less than 90, and (vii) a spectrum whose intensity decreases from its maximum value in the orange to red region of the spectrum to about 50% of said maximum value at a wavelength in a range from about 645 nm to about 695 nm and has a CRI Ra greater than or equal to 95, and CRI R1 to CRI R15 greater than or equal to 90.

Although the present invention has been particularly described with reference to certain embodiments thereof, it should be readily apparent to those of ordinary skill in the art that changes and modifications in the form and details may be made without departing from the spirit and scope of the invention.

What is claimed is:

1. A full spectrum white light emitting device comprising:
    photoluminescence materials which generate light with a peak emission wavelength from 490 nm to 680 nm; and
    a broadband solid-state excitation source that generates broadband excitation light with a dominant wavelength from 420 nm to 480 nm and a FWHM of at least 30 nm,
    wherein the device generates white light having an intensity that decreases from a maximum value in the orange to red region of the spectrum to 50% of said maximum value at a wavelength from 625 nm to 695 nm.

2. The light emitting device of claim 1, wherein said white light has an intensity that decreases to 50% of said maximum value at a wavelength from 625 nm to 665 nm.

3. The light emitting device of claim 1, wherein said white light has an intensity that decreases to 50% of said maximum value at a wavelength from 645 nm to 665 nm.

4. The light emitting device of claim 1, wherein said white light has a CRI Ra of at least 80.

5. The light emitting device of claim 1, wherein said white light has a CRI Ra of at least 90.

6. The light emitting device of claim 1, wherein said white light has a CRI Ra of at least 95.

7. The light emitting device of claim 1, wherein over a wavelength range from 430 nm to 530 nm, a maximum percentage intensity deviation of said white from the intensity of light of a black-body curve or CIE Standard Illuminant D of the same color temperature is less than 60%.

8. The light emitting device of claim 7, wherein said maximum percentage intensity deviation of light emitted by the device is less than at least one of 50%, 40%, 30%, 20% and 10%.

9. The light emitting device of claim 1, wherein said white light has a CAF that is within 5% a black-body curve or CIE Standard Illuminant D of the same color temperature.

10. The light emitting device of claim 1, wherein the photoluminescence materials comprise at least one or a combination of photoluminescence materials which generates light with a peak emission wavelength from 600 nm to 660 nm.

11. The light emitting device of claim 1, wherein said white light has a Correlated Color Temperature from 2700K to 3000K and the device has a lumen efficacy of at least 102 lm/W.

12. The light emitting device of claim 1, wherein said white light has a Correlated Color Temperature from 4000K to 6800K and the device has a lumen efficacy of at least 110 lm/W.

13. The light emitting device of claim 1, wherein the broadband excitation light is composed of multiple narrowband blue light emissions having different wavelengths.

14. The light emitting device of claim 13, wherein the broadband solid-state excitation source comprises multiple narrowband solid-state light sources.

15. The light emitting device of claim 12, wherein the broadband blue solid-state excitation source comprises a solid-state light source having multiple different quantum wells.

* * * * *

UNITED STATES PATENT AND TRADEMARK OFFICE
CERTIFICATE OF CORRECTION

PATENT NO. : 11,127,721 B2
APPLICATION NO. : 16/903251
DATED : September 21, 2021
INVENTOR(S) : Yi-Qun Li, Xianglong Yuan and Jun-Gang Zhao It is certified that error appears in the above-identified patent and that said Letters Patent is hereby corrected as shown below:

In the Claims

Column 26, Line 15, Claim 9:
"a CAF that is within 5% a black-body curve"

Should read:
"a CAF that is within 5% of a black-body curve"

Column 26, Lines 18-19, Claim 10:
"photoluminescence materials comprise at least one or a combination of photoluminescence materials"

Should read:
"photoluminescence materials comprise at least one of or a combination of photoluminescence materials"

Signed and Sealed this
Twenty-sixth Day of April, 2022

Katherine Kelly Vidal
*Director of the United States Patent and Trademark Office*